US006218547B1

(12) United States Patent
Teuber et al.

(10) Patent No.: US 6,218,547 B1
(45) Date of Patent: Apr. 17, 2001

(54) 1-PHENYL-BENZIMIDAZOLE COMPOUNDS AND THEIR USE AS GABA-$_A$ RECEPTOR MODULATORS

(75) Inventors: Lene Teuber; Frank Watjen, both of Glostrup (DK)

(73) Assignee: NeuroSearch A/S, Glostrup (DK)

( * ) Notice: Subject to any disclaimer, the term of this patent is extended or adjusted under 35 U.S.C. 154(b) by 0 days.

(21) Appl. No.: 09/269,643

(22) PCT Filed: Oct. 21, 1997

(86) PCT No.: PCT/DK97/00462

§ 371 Date: Mar. 31, 1999

§ 102(e) Date: Mar. 31, 1999

(87) PCT Pub. No.: WO98/17651

PCT Pub. Date: Apr. 30, 1998

(30) Foreign Application Priority Data

Oct. 21, 1996  (DK) .................................................. 1157/96

(51) Int. Cl.$^7$ ..................... C07D 235/02; C07D 235/04; C07D 403/02; A61K 31/4184; A61K 31/445

(52) U.S. Cl. ..................... 548/304.4; 514/322; 514/338; 514/394; 546/199; 548/306.1; 548/309.7; 548/310.1

(58) Field of Search ............................. 548/306.1, 309.7, 548/310.1, 304.4, 304.7; 514/338, 322, 394; 546/199

(56) References Cited

U.S. PATENT DOCUMENTS 5,158,969 * 10/1992 Olesen et al. ........................ 514/419
5,360,809 * 11/1994 Axelsson et al. .................... 514/338
5,554,630 *  9/1996 Teuber et al. ....................... 514/338
5,554,632 *  9/1996 Teuber et al. ....................... 514/338

FOREIGN PATENT DOCUMENTS

| 0563001 | 9/1993 | (EP) . |
| 0616807 | 9/1994 | (EP) . |
| 9633191 | 10/1996 | (WO) . |
| 9633192 | 10/1996 | (WO) . |
| 9633194 | 10/1996 | (WO) . |

\* cited by examiner

*Primary Examiner*—Floyd D. Higel
(74) *Attorney, Agent, or Firm*—Birch, Stewart, Kolasch & Birch, LLP

(57) ABSTRACT

The present invention relates to novel benzimidazole compounds, represented by general formula (I) in which o is 0, 1, 2 or 3; $R^1$ represents an alkyl group, a phenyl group, or a monocyclic heterocyclic group, which groups may be substituted one or more times with substituents selected from alkyl, cycloalkyl, cycloalkyl-alkyl, alkoxy, halogen, trifluoromethyl, cyano, amino and nitro; or $R^1$ represents a cyano group or a group of the formula -alkyl-$CO_2R^2$, alkenyl-$CO_2R^2$, —CO—$R^2$, —$CO_2(CH_2)_mR^2$, or —$C(R^3)$=N—$OR^2$, $R^{11}$ represents a group of formula —$CO_2$—$R^9$, or $R^{11}$ represents a group of general formula (II) in which n is 0, 1, 2 or 3; or $R^{11}$ may represent a group of general formula (III), in which n is 0, 1, 2 or 3; the novel compounds of the invention are useful in the treatment of central nervous system diseases and disorders, which are responsive to modulation of the $GABA_A$ receptor complex, such as for example anxiety, sleep disorders, anaestesia, memory disorders, and epilepsy or other convulsive disorders.

12 Claims, No Drawings

1-PHENYL-BENZIMIDAZOLE COMPOUNDS AND THEIR USE AS GABA-$_A$ RECEPTOR MODULATORS

This application is the national phase under 35 U.S.C. §371 of PCT International Application No. PCT/DK97/00462 which has an International filing date of Oct. 21, 1997 which designated the United States of America.

TECHNICAL FIELD

The present invention relates to novel benzimidazole compounds, pharmaceutical compositions containing these compounds, methods of treating therewith, and to method of preparing such benzimidazole compounds. The novel compounds of the invention are useful in the treatment of central nervous system diseases and disorders, which are responsive to modulation of the GABA$_A$ receptor complex, such as for example anxiety, sleep disorders, anaestesia, memory disorders, and epilepsy or other convulsive disorders.

BACKGROUND ART

GABA$_A$ receptors for γ-aminobutyric acid (GABA) are the most abundant inhibitory receptors in the mammalian brain. The GABA$_A$ receptors are structurally constituted as macromolecular heteropentameric assemblies (combinations of α, β, and γ/δ protein subunits). Several subtypes of such GABA$_A$ receptors have been described by techniques of modern molecular biology.

Each GABA$_A$ receptor complex comprises a chloride ion channel that controls chloride flux across the neuronal membrane, and multiple recognition sites for small modulatory molecules such as benzodiazepines, barbiturates, picrotoxin, and certain steroids. When GABA interacts with its receptor, the ion channel is opened, chloride influx is enhanced, the membrane is hyperpolarized and the cell becomes less responsive to excitatory stimuli. This GABA induced ion current can be regulated by diverse agents, including agents that interact with the benzodiazepine receptor or recognition site.

Agents that bind or interact with the modulatory sites on the GABA$_A$ receptor complex, such as for example the benzodiazepine receptor, can have either enhancing effect on the action of GABA, i.e. a positive modulatory effect of the receptor (agonists, partial agonists), an attenuating effect on the action of GABA, i.e.

negative modulation of the receptor (inverse agonists, partial inverse agonists), or they can block the effect of both agonists and inverse agonists by competitive block (antagonists or ligands without intrinsic activity).

Agonists generally produce muscle relaxant, hypnotic, sedative, anxiolytic, and/or anticonvulsant effects, while inverse agonists produce proconvulsant, anti-inebriant, and anxiogenic effects. Compounds with anxiolytic effects but without or with reduced muscle relaxant, hypnotic and sedative effects are characterised as partial agonists. Partial inverse agonists are considered to be useful as cognition enhancers.

Numerous compounds belonging to different chemical series of compounds having affinity for the benzodiazepine receptors have been synthesized during the last three decades. However, although the benzodiazepine receptor sites are still considered as very attractive biological sites for interfering with the CNS to treat various disorders and diseases, then nearly all previously synthesized compounds acting at these receptor sites have failed during clinical development because of unacceptable side effects.

Benzimidazole compounds for use in treatment of CNS disorders has been described in EP616807; Imidazole compounds as calcium channel blockers are described in EP 563001;

SUMMARY OF THE INVENTION

It is an object of the present invention to provide novel benzimidazole derivatives and pharmaceutically acceptable acid addition salts thereof, which are useful in the treatment of central nervous system disorders, diseases or ailments, which are responsive to the modulation of the GABA$_A$ receptor complex, and in particular the positive modulation of the GABA$_A$ receptor complex, and having a favorable pharmacodynamic and pharmacokinetic behavior.

Accordingly, the invention provides a chemical compound represented by the general formula (I):

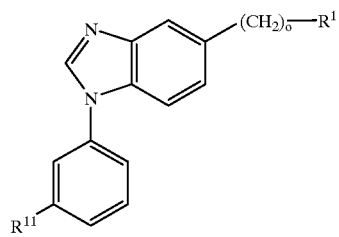

in which formula (I), o is 0, 1, 2 or 3;

$R^1$ represents an alkyl group, a phenyl group, or a monocyclic heterocyclic group, which groups may be substituted one or more times with substituents selected from alkyl, cycloalkyl, cycloalkyl-alkyl, alkoxy, halogen, trifluoromethyl, cyano, amino, and nitro;

or $R^1$ represents a cyano group, or a group of the formula -alkyl-CO$_2$R$^2$, alkenyl-CO$_2$R$^2$, —CO—R$^2$, —CO$_2$(CH$_2$)$_m$R$^2$, or —C(R$^3$)=N—OR$^2$, in which formulas m is 0, 1, 2 or 3;

$R^2$ and $R^3$ independently represents hydrogen, alkyl, alkenyl, alkynyl, phenyl, benzyl, a 5- or 6-membered heterocyclic group, which 5- or 6-membered heterocyclic group may optionally be substituted one or more times with substituents selected from alkyl, hydroxy, alkoxy, halogen, trifluoromethyl, cyano, amino, or nitro;

or $R^2$ and $R^3$ may independently represent a group of the formula —(CH$_2$)$_q$—NR$^4$R$^5$, —(CH$_2$)$_q$—CON(R$^4$R$^5$), —(CH$_2$)$_q$—CO$_2$R$^4$, or -alkyl-CO$_2$R$^4$, in which formulas $R^4$ and $R^5$ independently represent hydrogen or alkyl; and q is 0, 1, 2 or 3;

$R^{11}$ represents a group of the general formula —CO$_2$—R$^9$, wherein $R^9$ represents hydrogen or alkyl, which alkyl may optionally be substituted with a 5- or 6-membered heterocyclic group, which 5- or 6-membered heterocyclic group may optionally be substituted one or more times with substituents selected from alkyl, hydroxy, alkoxy, halogen, trifluoromethyl, cyano, amino, or nitro;

or $R^9$ may be a 5- or 6-membered heterocyclic group, which 5- or 6-membered heterocyclic group may optionally be substituted one or more times with substituents selected from alkyl, hydroxy, alkoxy, halogen, trifluoromethyl, cyano, amino, or nitro;

or R⁹ represent a group of the general formula -alkyl-N(R¹⁰R¹²), in which formula
R¹⁰ and R¹² independently represent hydrogen or alkyl;
or R¹¹ represents a group of general formula (II):

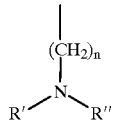

in which formula (II),
n is 0, 1, 2, or 3;
R' and R" each independently represents hydrogen or alkyl;
or R' and R" together with the N atom to which they are attached form a 5- to 7-membered heterocyclic ring, which heterocyclic ring may optionally comprise as a ring member, one oxygen atom, and/or one additional nitrogen atom, and/or a —CH═CH— chain;
and in which formula the 5- to 7-membered heterocyclic ring formed by R' and R" may optionally be substituted one ore more times with a group of the formula —(CH₂)$_p$X, wherein
p is 0, 1, 2 or 3;
X represents hydrogen, hydroxy, alkyl or alkenyl, which alkyl and alkenyl may optionally be substituted one or more times with a group of the formula —CO₂R⁶;
or X represents a group of the formula —CO—R⁶, —CO₂—R⁶, —CON—R⁶R⁷, or —COO—R⁶—NR⁷R⁸, in which formulas
R⁶, R⁷ and R⁸ independently represents hydrogen or alkyl;
or R¹¹ may represent a group of the general formula (III):

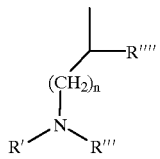

in which formula (III),
n is 0, 1, 2 or 3;
R' is hydrogen or alkyl;
R'" and R"" together with the atoms to which they are attached form a 5- to 7-membered heterocyclic ring, which heterocyclic ring may optionally comprise as a ring member, one oxygen atom, and/or one additional nitrogen atom, and/or a —CH═CH— chain;
and in which formula the 5- to 7-membered heterocyclic ring formed by R'" and R"" may optionally be substituted one ore more times with a group of the formula —(CH₂)$_p$X, wherein
p is 0, 1, 2 or 3;
X represents hydrogen, hydroxy, alkyl or alkenyl, which alkyl and alkenyl may optionally be substituted one or more times with a group of the formula —CO₂R⁶;
or X represents a group of the formula —CO—R⁶, —CO₂—R⁶, —CON—R⁶R⁷,
or —COO—R⁶—NR⁷R⁸, in which formulas
R⁶, R⁷ and R⁸ independently represents hydrogen or alkyl;

or a pharmaceutically acceptable salt thereof or an oxide thereof.

In another aspect, the invention provides pharmaceutical compositions comprising the novel benzimidazole compounds of the invention.

Still another object of the present invention is to provide novel methods of treatment using the novel benzimidazole compounds of the invention.

A further object of the present invention is to provide a method of preparing the novel pharmaceutical compositions of the invention.

Additional objects will be obvious from the following description, and others will be obvious to a person skilled in the art.

DETAILED DISCLOSURE OF THE INVENTION

Benzimidazole Derivatives

In its first aspect the invention provides novel benzimidazole derivatives. The chemical compounds of the invention may be characterized by the following general formula (I):

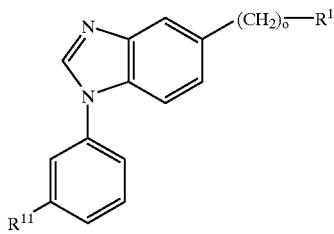

in which formula (I),
o is 0, 1, 2 or 3;
R¹ represents an alkyl group, a phenyl group, or a monocyclic heterocyclic group, which groups may be substituted one or more times with substituents selected from alkyl, cycloalkyl, cycloalkyl-alkyl, alkoxy, halogen, trifluoromethyl, cyano, amino, and nitro;
or R¹ represents a cyano group, or a group of the formula -alkyl-CO₂R², alkenyl-CO₂R², —CO—R², —CO₂(CH₂)$_m$R², or —C(R³)═N—OR², in which formulas
m is 0, 1, 2 or 3;
R² and R³ independently represents hydrogen, alkyl, alkenyl, alkynyl, phenyl, benzyl, a 5- or 6-membered heterocyclic group, which 5- or 6-membered heterocyclic group may optionally be substituted one or more times with substituents selected from alkyl, hydroxy, alkoxy, halogen, trifluoromethyl, cyano, amino, or nitro;
or R² and R³ may independently represent a group of the formula —(CH₂)$_q$—NR⁴R⁵, —(CH₂)$_q$—CON(R⁴R⁵), —(CH₂)$_q$—CO₂R⁴, or -alkyl-CO₂R⁴, in which formulas
R⁴ and R⁵ independently represent hydrogen or alkyl; and
q is 0, 1, 2 or 3;
R¹¹ represents a group of the general formula —CO₂—R⁹, wherein
R⁹ represents hydrogen or alkyl, which alkyl may optionally be substituted with a 5- or 6-membered heterocyclic group, which 5- or 6-membered heterocyclic group may optionally be substituted one or more times with substituents selected from alkyl, hydroxy, alkoxy, halogen, trifluoromethyl, cyano, amino, or nitro;
or R⁹ may be a 5- or 6-membered heterocyclic group, which 5- or 6-membered heterocyclic group may optionally be substituted one or more times with substituents selected from alkyl, hydroxy, alkoxy, halogen, trifluoromethyl, cyano, amino, or nitro;

or $R^9$ represent a group of the general formula -alkyl-$N(R^{10}R^{12})$, in which formula
$R^{10}$ and $R^{12}$ independently represent hydrogen or alkyl;

or $R^{11}$ represents a group of general formula (II):

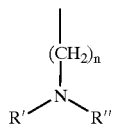

in which formula (II):
n is 0, 1, 2, or 3;
R' and R" each independently represents hydrogen or alkyl;
or R' and R" together with the N atom to which they are attached form a 5- to 7-membered heterocyclic ring, which heterocyclic ring may optionally comprise as a ring member, one oxygen atom, and/or one additional nitrogen atom, and/or a —CH=CH— chain;
and in which formula the 5- to 7-membered heterocyclic ring formed by R' and R" may optionally be substituted one ore more times with a group of the formula —$(CH_2)_pX$, wherein
p is 0, 1, 2 or 3;
X represents hydrogen, hydroxy, alkyl or alkenyl, which alkyl and alkenyl may optionally be substituted one or more times with a group of the formula —$CO_2R^6$;
or X represents a group of the formula —CO—$R^6$, —$CO_2$—$R^6$, —CON—$R^6R^7$, or —COO—$R^6$—$NR^7R^8$, in which formulas
$R^6$, $R^7$ and $R^8$ independently represents hydrogen or alkyl;

or $R^{11}$ may represent a group of the general formula (III):

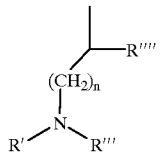

in which formula (III),
n is 0, 1, 2 or 3;
R' is hydrogen or alkyl;
R'" and R"" together with the atoms to which they are attached form a 5- to 7-membered heterocyclic ring, which heterocyclic ring may optionally comprise as a ring member, one oxygen atom, and/or one additional nitrogen atom, and/or a —CH=CH— chain;
and in which formula the 5- to 7-membered heterocyclic ring formed by R'" and R"" may optionally be substituted one ore more times with a group of the formula —$(CH_2)_pX$, wherein
p is 0, 1, 2 or 3;
X represents hydrogen, hydroxy, alkyl or alkenyl, which alkyl and alkenyl may optionally be substituted one or more times with a group of the formula —$CO_2R^6$;
or X represents a group of the formula —CO—$R^6$, —$CO_2$—$R^6$, —CON—$R^6R^7$, or —COO—$R^6$—$NR^7R^8$, in which formulas
$R^6$, $R^7$ and $R^8$ independently represents hydrogen or alkyl.

In a preferred embodiment, the chemical compound of the invention is characterized by the general formula (I) in wherein o is 0; and
$R^1$ represents a $C_{1-4}$-alkyl group, a cyano group, a phenyl group, a furanyl group, a tetrahydrofuranyl group, an isoxazolyl group, or an oxadiazolyl group;
or $R^1$ represents a $C_{1-4}$-alkenyl group substituted with $CO_2$—$C_{1-4}$-alkyl;
or $R^1$ represents a group of the formula —$CO_2R^2$, in which formula
$R^2$ represents hydrogen, a $C_{1-4}$-alkyl group, or a -$C_{3-5}$-cyclo-$C_{1-4}$-alkyl group, a benzyl group, a picolyl group, a pyrrolidyl group, a pyrrolidyl-methyl group, or a pyridyl group, which groups may be substituted with a $C_{1-3}$-alkyl group;
or $R^2$ may represent a group of the formula —$(CH_2)_p$—$NR^4R^5$, or —$(CH_2)_p$—CO—$NR^4R^5$, in which formulas
p is 0, 1, or 2;
$R^4$ and $R^5$ each independently represents hydrogen or a $C_{1-4}$-alkyl group;
or $R^2$ may represent a group of the formula —$C(R^3)$=N—$OR^4$, in which formula
$R^3$ and $R^4$ each independently represents hydrogen or a $C_{1-4}$-alkyl group;
or $R^1$ represents a group of the formula —$C(R^3)$=N—$OR^4$, in which formula
$R^3$ represents hydrogen or a $C_{1-4}$-alkyl group;
and $R^4$ represents hydrogen, a $C_{1-4}$-alkyl group, or a $C_{1-4}$-alkyl-$CO_2$—$C_{1-4}$-alkyl group.

In a more preferred embodiment, the chemical compound of the invention is characterized by the general formula (I) in wherein o is 0; and
$R^1$ is 3-furanyl, 3-tetrahydro-furanyl, 5-isoxazolyl, 3-cyclopropyl-1,2,4-oxadiazol-5-yl, —CHNOH, —C(CH$_3$)NOH, —C(CH$_3$)NO—CH$_3$, —C(CH$_3$)NO—C$_2$H$_5$, —C(CH$_3$)NO-isopropyl, —C(CH$_3$)NO-t-butyl, —C(CH$_3$)NO—CH$_2$CO$_2$CH$_3$, —C(CH$_3$)NO—CH$_2$CO$_2$C$_2$H$_5$, —CHNO—C(CH$_3$)$_2$CO$_2$CH$_3$, —C(CH$_3$)NO—C(CH$_3$)$_2$CO$_2$CH$_3$, —C(CH$_3$)NO—C(CH$_3$)$_2$CO$_2$C$_2$H$_5$, —C(CH$_3$)$_2$CO$_2$CH$_3$, —C(CH$_3$)$_2$CO$_2$C$_2$H$_5$, —CO$_2$CH$_3$, —CO$_2$C$_2$H$_5$, —CO$_2$CH(CH$_3$)$_2$, —CO$_2$(CH$_2$)$_2$N(CH$_3$)$_2$, —CO$_2$(CH$_2$)$_2$N(C$_2$H$_5$)$_2$, —CO$_2$—CH$_2$-cyclopropyl, (N,N-diethyl-carboxamido)-methyl, 3-picolyl, or 1-methyl-2-pyrrolidyl-methyl.

In another preferred embodiment, the chemical compound of the invention is characterized by the general formula (I) in wherein o is 1, 2 or 3; and
$R^1$ represents a phenyl group, or a group of the formula —$CO_2R^4$, in which formula
$R^4$ represents hydrogen or a $C_{1-4}$-alkyl group.

In a more preferred embodiment, the chemical compound of the invention is characterized by the general formula (I) in wherein o is 1, 2 or 3; and
$R^1$ is —CO$_2$CH$_3$, —CO$_2$C$_2$H$_5$, —CO$_2$CH(CH$_3$)$_2$, —CO$_2$CH$_2$-cyclopropyl, —CHNO—CH$_3$, —CHNO—C$_2$H$_5$, —CHNO—C$_3$H$_7$, —CHNO-isopropyl, —C(CH$_3$)NO—CH$_3$, —C(CH$_3$)NO—C$_2$H$_5$, —C(CH$_3$)NO—C$_3$H$_7$, —C(CH$_3$)NO-isopropyl, —C(CH$_3$)NO—C$_4$H$_9$, —C(CH$_3$)NO-tert. butyl, —CO$_2$CH$_2$N(CH$_3$)$_2$, —CO$_2$CH$_2$N(C$_2$H$_5$)$_2$, 2(dimethyl-amino)ethyl, (N,N-diethyl-carboxamido)-methyl, or 3-picolyl.

In another preferred embodiment, the chemical compound of the invention is characterized by the general formula (I) in wherein $R^{11}$ represents a $C_{1-4}$-alkyl-oxycarbonyl group, an amino-$C_{1-4}$-alkyl-oxycarbonyl group, an N—$C_{1-4}$-alkyl-amino-$C_{1-4}$-alkyl-oxycarbonyl group, an N,N-di-($C_{1-4}$-alkyl)-amino-$C_{1-4}$-alkyl-oxycarbonyl group, a piperidinyl group, an oxycarbonyl-piperidinyl group, a pyrrolidinyl group, a pyrrolidinyl-$C_{1-4}$-alkyl group, a piperazinyl group, a morpholinyl group, a homopiperazinyl group, a pyridyl group, a tetrahydropyridyl group, a picolyl group, a oxycarbonyl-picolyl group, which groups may optionally be substituted one or more times with substituents selected from $C_{1-4}$-alkyl, $C_{1-4}$-alkyl-oxy, $C_{1-4}$-alkyl-oxycarbonyl, $C_{1-4}$-alkyl-oxycarbonyl-$C_{1-4}$-alkyl, $C_{1-4}$-alkenyl-oxycarbonyl-$C_{1-4}$-alkyl, $C_{1-4}$-alkenyl-(oxycarbonyl-$C_{1-4}$-alkyl)$_2$, acetyl, hydroxy-$C_{1-4}$-alkyl, carboxamido, N-$C_{1-4}$-alkyl-carboxamido-$C_{1-4}$-alkyl, or N,N-di-$C_{1-4}$-alkyl-carboxamido-$C_{1-4}$-alkyl.

In a more preferred embodiment, the chemical compound of the invention is characterized by the general formula (I) in wherein $R^{11}$ is 1-piperidinyl, 1-pyrrolidinyl, 4-methyl-1-piperazinyl, 1-methyl-3-piperidinyl, (1-methyl-4-piperidinyl)oxycarbonyl, (1-methyl-3-piperidinyl) oxycarbonyl, 2-picolyl-oxycarbonyl, 3-picolyl-oxycarbonyl, 4-morpholinyl, 1-acetyl-4-piperazinyl, 4-(2-hydroxyethyl)piperazin-1-yl, (1-pyrrolidinyl) methyl, 4-methylhomopiperazin-1-yl, 1-methyl-1,2,3, 6-tetrahydropyrid-5-yl, 4-(N,N-diethyl-carboxamidomethyl)-piperazin-1-yl, 4-(N,N-dimethyl-carboxamidomethyl)-piperazin-1-yl, 4-(methoxycarbonylmethyl)-1-piperazinyl, 4-(ethoxycarbonylmethyl)-1-piperazinyl, 4-(t-butoxycarbonylmethyl)-1-piperazinyl, 4-(diethylcarboxamido-methyl)piperazin-1-yl, 4-(2,2-bis(ethoxycarbonyl)ethenyl)piperazin-1-yl, 4-(2-methoxycarbonyl-ethenyl)piperazin-1-yl, methoxycarbonyl, ethoxycarbonyl, 2-amino-ethoxycarbonyl, 2-(N-methylamino)ethoxycarbonyl, or 2-(N,N-dimethylamino)ethoxycarbonyl.

In a most preferred embodiment the chemical compound of the invention is

5-Cyano-1-(3-(1-piperidyl)phenyl)benzimidazole (compound 3a);
5-Cyano-1-(3-(1-pyrrolidinyl)phenyl)benzimidazole (compound $3a_2$);
5-Cyano-1-(3-(4-methyl-1-piperazinyl)phenyl) benzimidazole (compound $3a_3$);
5-Cyano-1-(3-(1-methyl-3-piperidinyl)phenyl) benzimidazole (compound $3a_4$);
5-Cyano-1-(3-(4-morfolinyl)phenyl benzimidazole (compound $3a_5$);
5-Formyl-1-(3-(1-piperidinyl)phenyl)benzimidazole oxime (compound $3b_1$);
5-Formyl-1-(3-(1-pyrrolidinyl)phenyl)benzimidazole oxime (compound $3b_2$):
5-Formyl-1-(3-(4-methyl-1-piperazinyl)phenyl) benzimidazole oxime (compound $3b_3$);
5-Formyl-1-(3-(1-methyl-3-piperidinyl)phenyl) benzimidazole oxime (compound $3b_4$);
5-Formyl-1-(3-(1-piperidinyl)phenyl)benzimidazole O-isopropyl oxime (compound 3c);
5-Formyl-1-(3-(1-piperidinyl)phenyl)benzimidazole O-methyl oxime (compound 3d);
5-Acetyl-1-(3-(1-acetylpiperazin-4-yl)phenyl) benzimidazole oxime (compound $3e_1$);
5-Acetyl-1-(3-(4-(2-hydroxyethyl)piperazin-1-yl) phenylbenzimidazole oxime (compound $3e_2$);
5-Acetyl-1-(3-(4-(2-hydroxyethyl)piperazin-1-yl) phenylbenzimidazole O-ethyl oxime (compound $3f_1$);
5-Acetyl-1-(3-(4-methylpiperazin-1-yl)phenyl) benzimidazole O-ethyl oxime (compound $3f_2$);
5-Acetyl-1-(3-(1-pyrrolidinylmethyl)phenyl)benzimidazole O-ethyl oxime (compound $3f_3$);
5-Acetyl-1-(3-(4-methylhomopiperazin-I-yl)benzimidazole O-ethyl oxime (compound $3f_4$);
5-Acetyl-1-(3-(1-pyrrolidinyl)phenyl)benzimidazole O-ethyl oxime (compound $3f_5$);
5-Acetyl-1-(3-(1-piperidinyl)phenyl)benzimidazole O-ethyl oxime (compound $3f_6$);
5-Acetyl-1-(3-(1-methyl-3-piperidinyl)phenyl) benzimidazole O-methyl oxime (compound $3f_7$);
5-Acetyl-1-(3-(1-methyl-1,2,3,6-tetrahydropyrid-5-yl) phenyl)benzimidazole O-ethyl oxime (compound $3f_8$);
5-Acetyl-1-(3-(1-methylpiperidin-3-yl)phenyl) benzimidazole O-isopropyl oxime (compound $3g_1$);
5-Acetyl-1-(3-(4-(2-hydroxyethyl)piperazin-1-yl)phenyl) benzimidazole O-isopropyl oxime (compound $3g_2$);
5-Acetyl-1-(3-(4-acetylpiperazin-1-yl)phenyl) benzimidazole O-isopropyl oxime (compound $3g_3$);
5-Acetyl-1-(3-(4-(2-hydroxyethyl)piperazin-1-yl)phenyl) benzimidazole O-t-butyl oxime (compound 3h);
5-(3-Furanyl)-1-(3-(4-methylpiperazin-1-yl)phenyl) benzimidazole (compound $3i_1$);
5-(3-Furanyl)-1-(3-(1-methylpiperidin-3-yl)phenyl) benzimidazole (compound $3i_2$);
5-(3-Furanyl)-1-(3-(4-(2-hydroxyethyl)piperazin-1-yl) phenyl)benzimidazole (compound $3i_3$);
5-(3-Furanyl)-1-(3-(4-(diethylcarboxamidomethyl) piperazin-1-yl)phenyl)benzimidazole (compound $3i_4$);
5-Phenyl-1-(3-(4-methylpiperazin-1-yl)phenyl) benzimidazole (compound $3j_1$):
5-Phenyl-1-(3-(1-methylpiperidin-3-yl)phenyl) benzimidazole (compound $3j_2$):
5-(3-Cyclopropyl-1,2,4-oxadiazol-5-yl)-1-(3-(1-methylpiperidin-3-yl)phenyl)-benzimidazole (compound 3k);
5-t-Butyl-1-(3-(1-methylpiperidin-3-yl)phenyl) benzimidazole (compound 3l);
5-(Ethoxycarbonyl)-1-(3-(1-methylpiperidin-3-yl)phenyl) benzimidazole (compound $4a_1$);
5-(Ethoxycarbonyl)-1-(3-(4-methylpiperazin-1-yl)phenyl) benzimidazole (compound $4a_2$);
5-(Ethoxycarbonyl)-1-(3-(4-(2-hydroxyethyl)piperazin-1-yl)phenyl)benzimidazole (compound $4a_3$);
5-(Ethoxycarbonyl)-1-(3-(1-acetylpiperazin-4-yl)phenyl) benzimidazole (compound $4a_4$);
5-(Ethoxycarbonyl)-1-(3-(4-(methoxycarbonylmethyl) piperazin-1-yl)phenyl)-benzimidazole (compound $4a_5$);
5-(Ethoxycarbonyl)-1-(3-(4-(ethoxycarbonylmethyl) piperazin-1-yl)phenyl)-benzimidazole (compound $4a_6$);
5-(2-(Ethoxycarbonyl)ethenyl)-1-(3-(1-piperidyl)phenyl) benzimidazole (compound $4b_1$);
5-(2-(Ethoxycarbonyl)ethenyl)-1-(3-(4-methylpiperazin-1-yl)phenyl)benzimidazole (compound $4b_2$);
5-(2-(Ethoxycarbonyl)ethenyl)-1-(3-(4-morfolinyl)phenyl) benzimidazole (compound $4b_3$);
5-(2-(Methoxycarbonyl)ethenyl)-1-(3-(4-methylpiperazin-1-yl)phenyl)benzimidazole (compound $4c_1$);
5-(2-(Methoxycarbonyl)ethenyl)-1-(3-(4-morfolinyl) phenyl)benzimidazole (compound $4c_2$);

5-(Methoxycarbonyl)-1-(3-(1-acetylpiperazin-3-yl)phenyl) benzimidazole (compound $4d_1$);

5-(Methoxycarbonyl)-1-(3-(4-methylpiperazin-1-yl) benzimidazole (compound $4d_2$);

4-(Methoxycarbonyl)-1-(3-(4-methoxycarbonylmethyl) piperazin-1-yl)benzimidazole (compound $4d_3$);

5-(Methoxycarbonyl)-1-(3-(4-(diethylcarboxamidemethyl) piperazin-1-yl)phenyl)-benzimidazole (compound $4d_4$);

5-(Methoxycarbonyl)-1-(3-(4-morfolinyl)phenyl) benzimidazole (compound $4d_5$);

5-(i-Propyloxycarbonyl)-1-(3-(1-piperidinyl)phenyl) benzimidazole (compound $4e_1$);

5-(i-Propyloxycarbonyl)-1-(3-(1-pyrrolidinyl)phenyl) benzimidazole (compound $4e_2$);

5-(i-Propyloxycarbonyl)-1-(3-(4-methylpiperazin-1-yl) phenyl)benzimidazole (compound $4e_3$);

5-(i-Propyloxycarbonyl)-1-(3-(4-morfolinyl)phenyl) benzimidazole (compound $4e_4$);

5-(Cyclopropylmethyloxycarbonyl)-1-(3-(1-methylpiperidin-3-yl)phenyl)benzimidazole (compound 4f);

5-(Benzyloxycarbonyl)-1-(3-(1-methylpiperidin-3-yl) phenyl)benzimidazole (compound 4g);

5-(3-Picolyloxycarbonyl)-1-(3-(1-methylpiperidin-3-yl) phenyl)benzimidazole (compound 4h);

5-(2-((Dimethylamino)ethyl)oxycarbonyl)-1-(3-(1-acetylpiperazin-4-yl)phenyl)-benzimidazole (compound 4i);

5-((2-(Dimethylamino)ethyl)oxycarbonyl)-1-(3-(4-(ethoxycarbonylmethyl)piperazin-1-yl)phenyl) benzimidazole (compound 4j);

5-((N,N-Diethylcarboxamido)methyloxycarbonyl)-1-(3-(4-ethoxycarbonylmethyl)-piperazin-1-yl)phenyl) benzimidazole (compound $4k_1$);

5-((N,N-diethylcarboxamido)-methyloxycarbonyl)-1-(3-(1-acetylpiperazin-4-yl)phenyl)benzimidazole (compound $4k_2$);

5-(Methoxycarbonylmethyl)-1-(3-(4-methylpiperazin-1-yl) phenyl)benzimidazole (compound $4l_1$);

5-(Ethoxycarbonylmethyl)-1-(3-(4-methylpiperazin-1-yl) phenyl)benzimidazole (compound $4l_2$);

5-(Methoxycarbonyl)-1-(3-(4-morfolinyl)phenyl) benzimidazole (compound $4l_3$);

5-(Ethoxycarbonyl)-1-(3-(4-morfolinyl)phenyl) benzimidazole (compound $4l_4$);

5-((1-Methylpyrrolidin-2-yl)methoxycarbonyl)-1-(3-(4-(ethoxycarbonylmethyl)-piperazin-1-yl)phenyl) benzimidazole (compound 4m);

5-Acetyl-1-(3-(1-methyl-4-piperidyloxycarbonyl)phenyl) benzimidazole O-isopropyl oxime (compound $5a_1$);

5-Acetyl-1-(3-(1-methyl-3-piperidyloxycarbonyl)phenyl) benzimidazole O-i-propyl oxime (compound $5a_2$);

5-Acetyl-1-(3-(2-picolyloxycarbonyl)phenyl)benzimidazole O-i-propyl oxime (compound $5a_3$);

5-Acetyl-1-(3-(1-methylpiperidin-3-yl)phenyl) benzimidazole O-(ethoxycarbonyl-methyl) oxime (compound $5b_1$);

5-Acetyl-1-(3-(1-methylpiperidin-3-yl)phenyl) benzimidazole O-(methoxycarbonylmethyl) oxime (compound $5b_2$);

5-Acetyl-1-(3-(1-methylpiperidin-3-yl)phenyl) benzimidazole O-(methoxycarbonyl-(dimethyl)methyl) oxime (compound $5b_3$);

5-Acetyl-1-(3-(4-(2-hydroxyethyl)piperazin-1-yl)phenyl) benzimidazole O-(methoxy-carbonylmethyl) oxime (compound $5c_1$);

5-Acetyl-1-(3-(4-(2-hydroxyethyl)piperazin-1-yl)phenyl) benzimidazol O-(ethoxy-carbonylmethyl) oxime (compound $5c_2$);

5-Acetyl-1-(3-(4-(2-hydroxyethyl)piperazin-1-yl)phenyl) benzimidazole O-(ethoxy-carbonyl(dimethyl)methyl) oxime (compound $5c_3$);

5-Acetyl-1-(3-(4-(ethoxycarbonylmethyl)piperazin-1-yl) phenyl)benzimidazole oxime (compound $5d_1$);

5-Acetyl-1-(3-(4-(ethoxycarbonylmethyl)piperidin-1-yl) phenyl)benzimidazole O-ethyl oxime (compound $5d_2$);

5-Acetyl-1-(3-(1-acetylpiperazin-4-yl)phenyl) benzimidazole O-(methoxycarbonyl-(dimethyl)methyl) oxime (compound $5e_1$);

5-Acetyl-1-(3-(1-acetylpiperazin-4-yl)phenyl) benzimidazole O-(methoxycarbonyl-methyl) oxime (compound $5e_2$);

5-Acetyl-1-(3-(4-morfolinyl)phenyl)benzimidazole O-(methoxycarbonylmethyl) oxime (compound $5e_3$);

5-Acetyl-1-(3-(4-(methoxycarbonylmethyl)piperazin-1-yl) phenyl)benzimidazole O-i-propyl oxime (compound $5f_1$);

5-acetyl-1-(3-(4-(2,2-bis(ethoxycarbonyl)ethenyl) piperazin-1-yl)phenyl)benzimidazole O-i-propyl oxime (compound $5f_2$);

5-Formyl-1-(3-(4-methylpiperazin-1-yl)phenyl) benzimidazole O-(methoxycarbonyl-(dimethyl)methyl) oxime (compound $5g_1$);

5-Formyl-1-(3-(4-morfolinyl)phenyl)benzimidazole O-(methoxycarbonyl)dimethyl)-methyl) oxime (compound $5g_2$);

5-(5-Isoxazolyl)-1-(3-(methoxycarbonyl)phenyl) benzimidazole (compound $6a_1$);

5-(5-Isoxazolyl)-1-(3-ethoxycarbonyl)phenyl benzimidazole (compound $6a_2$);

1-(3-Ethoxycarbonyl)phenyl-5-phenylbenzimidazole (compound $6b_1$);

5-Phenyl-1-(3-(4-ethoxycarbonylmethyl)piperazin-1-yl) phenyl)benzimidazole (compound $6b_2$);

5-Phenyl-1-(3-(2-picolyloxycarbonyl)phenyl) benzimidazole (compound $6b_3$);

5-Phenyl-1-(3-(3-picolyloxycarbonyl)phenyl) benzimidazole (compound $6b_4$);

5-Phenyl-1-(3-(1-methylpiperid-3-yloxycarbonyl)phenyl) benzimidazole (compound $6b_5$);

5-Phenyl-1-(3-((1-methylpiperid-4-yl)oxycarbonyl)phenyl) benzimidazole (compound $6b_6$);

5-(3-furanyl)-1-(3-(ethoxycarbonyl)phenyl)benzimidazole (compound $6c_1$);

5-(3-Tetrahydrofuranyl)-1-(3-(ethoxycarbonyl)phenyl) benzimidazole (compound $6c_2$);

5-(3-Furanyl)-1-(3-(4-(ethoxycarbonylmethyl)piperazin-1-yl)phenyl)benzimidazole (compound $6c_3$);

5-(3-Furanyl)-1-(3-(4-(t-butoxycarbonyl)piperazin-1-yl) phenyl)benzimidazole (compound $6c_4$);

5-(3-Furanyl)-1-(3-(4-(methoxycarbonylmethyl)piperazin-1-yl)phenyl)benzimidazole (compound $6c_5$);

5-(3-Furanyl)-1-(3-(4-(2,2-bis(ethoxycarbonyl)ethenyl) piperazin-1-yl)phenyl)benzimidazole (compound $6c_6$);

5-(3-Furanyl)-1-(3-(4-(2-(methoxycarbonyl)ethenyl) piperazin-1-yl)phenyl)benzimidazole (compound $6c_7$);

5-(3-Furanyl)-1-(3-(2-(dimethylamino)ethyloxycarbonyl) phenyl)benzimidazole (compound $6c_8$);

5-Acetyl-1-[3-(1-methyl-1,2,3,6-tetrahydropyrid-5-yl) phenyl]-benzimidazole (compound 7); or 5-Acetyl-1-[3-(1-methylpiperidin-3-yl)phenyl]-benzimidazole (compound 9);

or a pharmaceutically acceptable salt thereof, or an oxide thereof.

Definition of Substituents

In the context of this invention halogen represents fluorine, chlorine, bromine and iodine.

In the context of this invention alkyl designates a straight chain or a branched chain containing of from one to eight carbon atoms ($C_1$–$C_8$-alkyl), including but not limited to methyl, ethyl, propyl, isopropyl, butyl, isobutyl, tertiary butyl, pentyl and hexyl, or a cyclic alkyl containing of from three to seven carbon atoms ($C_3$–$C_7$ cycloalkyl), including but not limited to cyclopropyl, cyclobutyl, cyclopentyl, and cyclohexyl. In a preferred embodiment of this invention alkyl represents a $C_1$–$C_4$ alkyl, preferably a $C_{1-3}$-alkyl, most preferred methyl, ethyl, propyl, isopropyl or t-butyl.

In the context of this invention alkenyl designates a group containing of from two to six carbon atoms ($C_2$–$C_6$ alkenyl), including at least one double bond. The chain may be straight or branched. In a preferred embodiment, the alkenyl group is ethenyl, 1-propenyl, 2-propenyl, 1-butenyl, 2-butenyl, or 3-butenyl.

In the context of this invention alkynyl designates a group containing of from two to six carbon atoms ($C_2$–$C_6$ alkynyl), including at least one triple bond. The chain may be straight or branched. In a preferred embodiment, the alkenyl group is ethynyl, 1-propynyl, 2-propynyl, 1-butynyl, 2-butynyl, or 3-butynyl.

In the context of this invention amino represents $NH_2$, NH-alkyl, or N-(alkyl)$_2$, wherein alkyl is as defined above.

In the context of this invention cycloalkyl-alkyl designates a cycloalkyl as defined above which is attached to an alkyl as also defined above, e.g. cyclopropylmethyl.

The alifatic cyclic rings formed by R' and R" or R" and R''' includes but are not limited to piperidinyl, tetrahydropyridinyl, tetrahydropyrimidinyl, hexahydropyrimidinyl, pyrrolidinyl, homopiperazinyl, morpholinyl, isoxazolidinyl, oxazolindinyl, piperazinyl, perhydroazepinyl, and perhydrooxazepinyl.

In the context of this invention aryl designates an aromatic hydrocarbon, such as phenyl or naphthyl.

In the context of this invention a monocyclic heteroaryl designates a 5- or 6-membered heterocyclic monocyclic group. Preferred monocyclic heteroaryl group includes oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidyl, 4-pyrimidyl, 5-pyrimidyl, 3-pyridazinyl, 4-pyridazinyl, 2-pyrazinyl, 1-pyrazolyl, 3-pyrazolyl, and 4-pyrazolyl.

In the context of this invention 5- or 6-membered ring containing at least one heteroatom includes but are not limited to furanyl, tetrahydrofuranyl ,pyrrolyl, pyrrolidyl, imidazolyl, oxadiazolyl, pyridyl, thienyl, isooxazolyl, pyrimidyl, pyrazole, In the context of this invention alkyl-oxy (alkoxy) designates an alkyl-O— where alkyl is as defined above.

In the context of this invention alkyl-oxycarbonyl (alkoxycarbonyl) designates an alkyl-O—CO— where alkyl is as defined above.

Steric Isomers

Some of the chemical compounds of the present invention exist in (+) and (−) forms as well as in racemic forms.

Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Moreover, being oximes, the chemical compounds of the invention may exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Pharmaceutically Acceptable Salts

The novel benzimidazole derivatives of the invention may be provided in any form suitable for the intended administration. Suitable forms include pharmaceutically (i.e. physiologically) acceptable salts.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt, of a chemical compound of the invention containing a carboxy group.

The chemical compound of the invention may be provided in solved or dissolved form together with a pharmaceutically acceptable solvents such as water, ethanol and the like. In general, solved forms are considered equivalent to dissolved forms for the purposes of this invention.

Pharmaceutical Compositions

In another aspect the invention provides novel pharmaceutical compositions comprising a therapeutically effective amount of the chemical compound of the invention. While a chemical compound of the invention for use in therapy may be administered in the form of the raw chemical compound, it is preferred to introduce the active ingredient, optionally in the form of a physiologically acceptable salt in a pharmaceutical composition together with one or more excipients, carriers and/or diluents.

In a preferred embodiment, the invention provides pharmaceutical compositions comprising the chemical compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions those suitable for oral, rectal, nasal, topical (including buccal and sub-lingual), vaginal or parenteral (including intramuscular, subcutaneous and intravenous) administration, or in a form suitable for administration by inhalation or insufflation.

The chemical compound of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Compositions containing ten (10) milligrams of active ingredient or, more broadly, 0.1 to one hundred (100) milligrams, per tablet, are accordingly suitable representative unit dosage forms.

The chemical compound of the present invention can be administrated in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Biological Activity and Methods of Treatment 4-aminobytyric acid (GABA) is the major inhibitory neurotransmitter which has been shown to act throughout both the central and peripheral nervous system. At present two types of GABA receptors are known, the $GABA_A$ and the $GABA_B$ receptors. Recent molecular biology has demonstrated that the $GABA_A$ receptors can be subdivided into numerous subreceptors consistant with the selective and or partial pharmacological effects observed with certain benzodiazepine receptor ligands as opposed to the unselective effects observed for the classical benzodiazepine receptor ligands such as for example diazepam.

Activation of GABA receptors leads to alternations in membrane potential (hyperpolarization), The $GABA_A$ receptors are associated with chloride influx through its associated and integrated chloride channel, whereas $GABA_B$ receptor activation indirectly alters potassium and calcium channels as well as modifies second messenger production. The $GABA_A$ recognition sites can be activated by GABA, muscimol, and isoguvacine for example, but not by $GABA_B$ agonists such as for example baclofen. The modulatory $GABA_A$ recognition site at the benzodiazepine receptor sites can be selectively radiolabelled with $^3$H-flunitrazepam.

The affinity of various potential ligands for the benzodiazepine receptor sites can thus be evaluated by estimating the ability of test compounds to displace $^3$H-flunitrazepam.

The compounds of the present invention may be useful for the treatment of disorders or diseases of a living animal body due to their modulatory effect on the benzodiazepine recognition site of the $GABA_A$ receptor complex. This property make the compounds of this invention extremely useful as muscle relaxants and in the treatment of convulsions, anxiety, sleep disorders, anaestesia, memory disorders as well as other disorders sensitive to modulation of the $GABA_A$ receptor.

Accordingly, the compounds of the present invention may be administered to a subject, including a human, in need of treatment, alleviation, or elimination of a disorder or disease associated with $GABA_A$ receptors. This includes especially convulsions, anxiety, sleep disorders, anaestesia, and memory disorders.

It is at present contemplated that a suitable dosage range is of from about 0.01 to about 100 mg per day, more preferred of from about 0.1 to about 50 mg per day, most prefferred of from about 0.1 to about 30 mg per day, dependent, however, upon the exact mode of administration, the form in which it is administered, the indication towards which the administration is directed, the subject involved and the body weight of the subject involved, and further the preference and experience of the physician or veterinarian in charge.

Methods of Preparation

The novel benzimidazole derivatives of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

EXAMPLES

The invention is further illustrated with reference to the following examples which are not intended to be in any way limiting to the scope of the invention as claimed.

The compounds of this invention represented by the following general formula

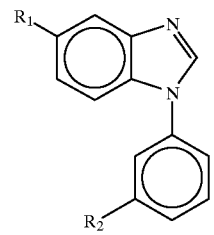

were prepared as outlined in the following scheme (Scheme 1):

Scheme 1

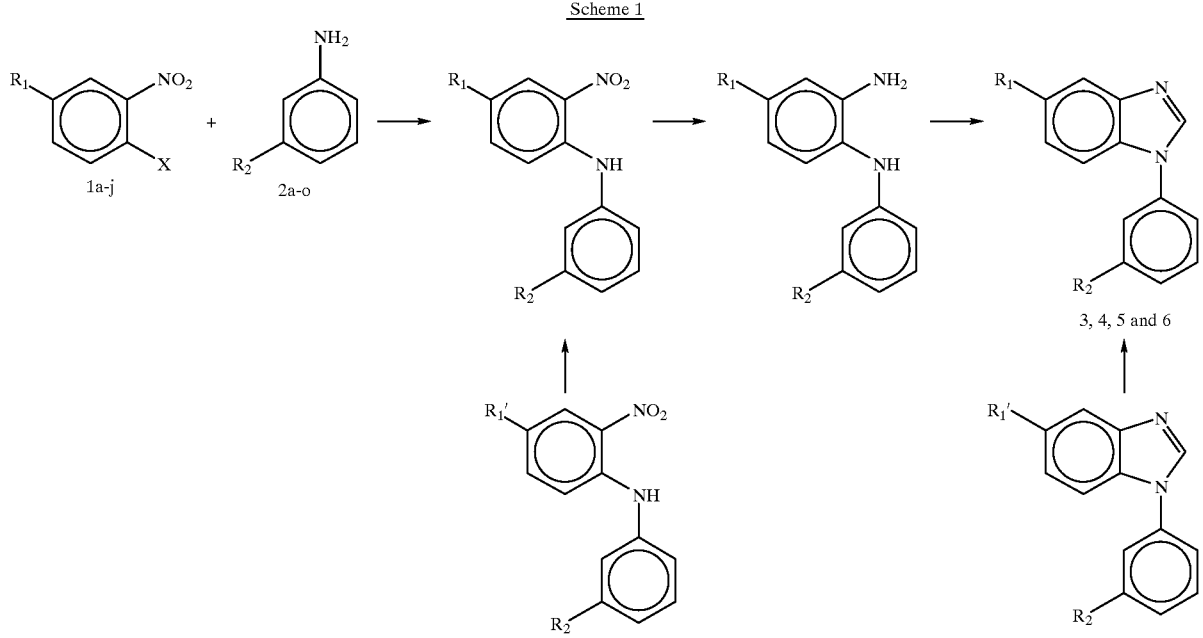

The starting materials (1 and 2) used for this preparation are listed in Tables 1–2, below.

TABLE 1

Compounds 1a–1i

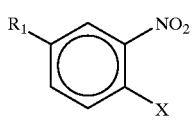

| Compound No. | R₁ | X | Method of preparation (Example) |
| --- | --- | --- | --- |
| 1a | CN | Cl | Commercially available |
| 1b | CH₃CO | F | 1 |
| 1c | CO₂Et | Cl | 2 |
| 1d | 3-furanyl | F | 3 |
| 1e | phenyl | F | 3 |
| 1f | t-Bu | F | 4 |
| 1g | I | F | 3 |
| 1h | CO₂CH₂CON(Et)₂ | Cl | 22 |
| 1i | CH₂COOH | F | 23 |

TABLE 2

Compounds 2a–2p

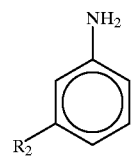

| Compound No. | R₂ | Method of preparation (Example) |
| --- | --- | --- |
| 2a | 1-piperidinyl | 5 |
| 2b | 1-pyrrolidinyl | 5 |
| 2c | 4-methyl-1-piperazinyl | 5 |
| 2d | 1-acetyl-4-piperazinyl | 6 |
| 2e | 4-(ethoxycarbonylmethyl)-1-piperazinyl | 6 |
| 2f | 4-((N,N-diethylcarboxamido)methyl)-1-piperazinyl | 6 |
| 2g | 1-(t-butoxycarbonyl)-4-piperazinyl | 7 |
| 2h | 1-methyl-4-homopiperazinyl | 7 |
| 2i | (1-pyrrolidinyl)methyl | 8 |
| 2j | 1-methyl-3-piperidinyl | 9 |
| 2k | 4-(2-hydroxyethyl)-1-piperazinyl | 6 |
| 2l | 4-(methoxycarbonylmethyl)-1-piperazinyl | 6 |
| 2m | 4-(2,2-bis(ethoxycarbonyl)ethenyl)piperazin-1-yl | 6 |
| 2n | 4-(2-(methoxycarbonyl)ethenyl)piperazin-1-yl | 6 |
| 2o | 4-morpholinyl | 5 |
| 2p | 3-pyridyl | 9a |

TABLE 3

Compounds 3a–l

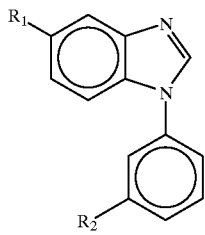

| Comp. No. | R₁ | R₂ | M.p. (° C.) | Starting Mater. | Met. of Prep. (Ex.) |
|---|---|---|---|---|---|
| 3a₁ | CN | 1-piperidinyl | 106–8 | 2a/1a | 10 |
| 3a₂ | CN | 1-pyrrolidinyl | 171–2 | 2b/1a | 10 |
| 3a₃ | CN | 4-methyl-1-piperazinyl | 177–9 | 2c/1a | 10 |
| 3a₄* | CN | 1-methyl-3-piperidinyl | 158–60 | 2j/1a | 10 |
| 3a₅ | CN | 4-morfolinyl | 163–5 | 2o/1a | 10 |
| 3b₁ | CHNOH | 1-piperidinyl | 213–4 | 3a₁ | 11 |
| 3b₂ | CHNOH | 1-pyrrolidinyl | 242–4 | 3a₂ | 11 |
| 3b₃ | CHNOH | 4-methyl-1-piperazinyl | 224–7 | 3a₃ | 11 |
| 3b₄ | CHNOH | 1-methyl-3-piperidinyl | 214–8 | 3a₄ | 11 |
| 3c | CHNOiPr | 1-piperidinyl | 127–8 | 3a₂ | 11 |
| 3d | CHNOMe | 1-piperidinyl | 107–8 | 3a₂ | 11 |
| 3e₁ | CH₃CNOH | 1-acetyl-4-piperazinyl | 240–1 | 2d/1b | 12 |
| 3e₂ | CH₃CNOH | 4-(2-hydroxyethyl)-piperazin-1-yl | 193–5 | 2k/1b | 12 |
| 3f₁* | CH₃CNOEt | 4-(2-hydroxyethyl)-piperazin-1-yl | oil | 2k/1b | 12 |
| 3f₂* | CH₃CNOEt | 4-methyl-1-piperazinyl | 62–3 | 2c/1b | 12 |
| 3f₃* | CH₃CNOEt | (1-pyrrolidinyl)methyl | 158–62 | 2i/1b | 12 |
| 3f₄* | CH₃CNOEt | 4-methylhomopiperazin-1-yl | 147–51 | 2h/1b | 12 |
| 3f₅ | CH₃CNOEt | 1-pyrrolidinyl | 118–20 | 2b/1b | 12 |
| 3f₆ | CH₃CNOEt | 1-piperidinyl | 88–9 | 2a/1b | 12 |
| 3f₇* | CH₃CNOEt | 1-methylpiperidin-3-yl | 112–14 | 2j/1b | 12 |
| 3f₈* | CH₃CNOEt | 1-methyl-1,2,3,6-tetrahydropyrid-5-yl | 227–233 | 2p/1b | 12a |
| 3g₁* | CH₃CNOiPr | 1-methylpiperidin-3-yl | 48–55 | 2j/1b | 12 |
| 3g₂* | CH₃CNOiPr | 4-(2-hydroxyethyl)-piperazin-1-yl | 165–9 | 2k/1b | 12 |
| 3g₃* | CH₃CNOiPr | 1-acetyl-4-piperazinyl | 160–3 | 2d/1b | 12 |
| 3h | CH₃CNOt-Bu | 4-(2-hydroxyethyl)-piperazin-1-yl | oil | 2k/1b | 12 |
| 3i₁ | 3-furanyl | 4-methylpiperazin-1-yl | 129–30 | 2c/1g | 13 |
| 3i₂ | 3-furanyl | 1-methylpiperidin-3-yl | 96–7 | 2j/1g | 13 |
| 3i₃ | 3-furanyl | 4-(2-hydroxyethyl)-piperazin-1-yl | 137–40 | 2k/1g | 13 |
| 3i₄ | 3-furanyl | 4-(N,N-diethyl-carboxamidomethyl)-piperazin-1-yl | 107–9 | 2f/1g | 13 |
| 3j₁ | phenyl | 4-methylpiperazin-1-yl | 131–2 | 2c/1g | 13 |
| 3j₂ | phenyl | 1-methylpiperidin-3-yl | 42–4 | 2j/1g | 13 |
| 3k* | 3-cyclopropyl-1,2,4-oxadiazol-5-yl | 1-methylpiperidin-3-yl | 184–90 | 4a₁ | 14 |
| 3l* | t-butyl | 1-methylpiperidin-3-yl | ~200 | 2j/1f | 15 |

*isolated as the hydrochloride.

TABLE 4

Compounds 4a–m

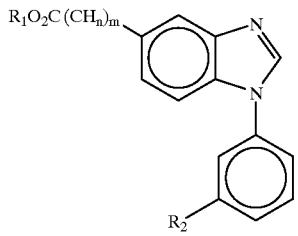

| Comp. No. | n | m | R₁ | R₂ | M.p. (° C.) | Start. Mat. | Met. Pre. (Ex) |
|---|---|---|---|---|---|---|---|
| 4a₁* | 0 | 0 | ethyl | 1-methylpiperidin-3-yl | hygroscop. | 2j/1c | 16 |
| 4a₂ | 0 | 0 | ethyl | 4-methylpiperazin-1-yl | 86–7 | 2c/1c | 16 |
| 4a₃* | 0 | 0 | ethyl | 4-(2-hydroxyethyl)-piperazin-1-yl | 233–6 | 2k/1c | 16 |
| 4a₄ | 0 | 0 | ethyl | 1-acetylpiperazin-4-yl | 155–6 | 2d/1c | 16 |
| 4a₅* | 0 | 0 | ethyl | 4-(methoxy-carbonylmethyl)-1-piprazinyl | 185–6 | 2l/1c | 16 |
| 4a₆* | 0 | 0 | ethyl | 4-(ethoxy-carbonylmethyl)-1-piperazinyl | 196–200 | 2e/1c | 16 |
| 4b₁ | 1 | 2 | ethyl | 1-piperidinyl | 85–7 | 3a₁ | 17 |
| 4b₂ | 1 | 2 | ethyl | 4-methylpiperazin-1-yl | 133–4 | 3a₃ | 17 |
| 4b₃ | 1 | 2 | ethyl | 4-morfolinyl | 197–200 | 3a₅ | 17 |
| 4c₁ | 1 | 2 | methyl | 4-methylpiperazin-1-yl | 138–40 | 3a₃ | 17 |
| 4c₂ | 1 | 2 | methyl | 4-morfolinyl | 137–9 | 3a₅ | 17 |
| 4d₁ | 0 | 0 | methyl | 1-acetyl-4-piperazinyl | 189–91 | 2d/1j | 18 |
| 4d₂ | 0 | 0 | methyl | 4-methyl-1-piperazinyl | 119–21 | 2c/1j | 18 |
| 4d₃ | 0 | 0 | methyl | 4-(methoxy-carbonylmethyl) piperazin-1-yl | oil | 2l/1j | 18 |
| 4d₄ | 0 | 0 | methyl | 4-(diethyl-carboxamido-methyl)-piperazin-1-yl | oil | 2f/1j | 18 |
| 4d₅ | 0 | 0 | methyl | 4-morfolinyl | 150–2 | 2o/1j | 18 |
| 4e₁ | 0 | 0 | i-propyl | 1-piperidinyl | 160–61 | 2a/1k | 19 |
| 4e₂ | 0 | 0 | i-propyl | 1-pyrrolidinyl | 170–72 | 2b/1k | 19 |
| 4e₃ | 0 | 0 | i-propyl | 4-methylpiperazinyl-1-yl | 110–11 | 2c/1k | 19 |
| 4e₄ | 0 | 0 | i-propyl | 4-morfolinyl | 173–4 | 2o/1k | 19 |
| 4f | 0 | 0 | cyclopropyl-methyl | 1-methylpiperidin-3-yl | 111–13 | 4a₁ | 20 |
| 4g* | 0 | 0 | benzyl | 1-methylpiperidin-3-yl | "90" | 4a₁ | 20 |
| 4h | 0 | 0 | 3-picolyl | 1-methylpiperidin-3-yl | oil | 4a₁ | 20 |
| 4i | 0 | 0 | 2-(dimethyl-amino)ethyl | 1-acetylpiperazin-4-yl | 101–3 | 2d | 21 |
| 4j | 0 | 0 | 2-(dimethyl-amino)ethyl | 4-(ethoxy-carbonylmethyl)-piperazin-1-yl | oil | 2e | 21 |
| 4k₁ | 0 | 0 | (N,N-diethyl-carboxamido)-methyl | 4-(ethoxy-carbonylmethyl)-piperazin-1-yl | 93–4 | 2e/1h | 22 |
| 4k₂ | 0 | 0 | (N,N-diethyl-carboxamido)-methyl | 1-acetylpiperazin-4-yl | oil | 2d/1h | 22 |
| 4l₁* | 2 | 1 | methyl | 4-methylpiperazin-1-yl | 140–42 | 2c/1i | 24 |
| 4l₂* | 2 | 1 | ethyl | 4-methylpiperazin-1-yl | 180–82 | 2c/1i | 24 |
| 4l₃* | 2 | 1 | methyl | 4-morfolinyl | 164–5 | 2o/1i | 24 |
| 4l₄* | 2 | 1 | ethyl | 4-morfolinyl | 168–9 | 2o/1i | 24 |
| 4m | 0 | 0 | 1-methyl-2-pyrrolidyl-methyl | 4-(ethoxy-carbonylmethyl)-piperazin-1-yl | oil | 2e | 25 |

*isolated as the hydrochloride.

TABLE 5

Compounds 5a–g

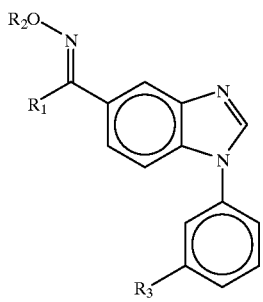

| Comp. No. | $R_1$ | $R_2$ | $R_3$ | M.p. (° C.) | Method of Prep. (Ex.) |
|---|---|---|---|---|---|
| $5a_1$ | $CH_3$ | i-Pr | (1-methyl-4-piperidyl)-oxycarbonyl | 106–7 | 26 |
| $5a_2$ | $CH_3$ | i-Pr | (1-methyl-3-piperidyl)-oxycarbonyl | 83–4 | 26 |
| $5a_3$ | $CH_3$ | i-Pr | (2-picolyl)-oxycarbonyl | 104–6 | 26 |
| $5b_1$* | $CH_3$ | $CH_2CO_2Et$ | 1-methyl-3-piperidyl | 73–5 | 27 |
| $5b_2$ | $CH_3$ | $CH_2CO_2Me$ | 1-methyl-3-piperidyl | 104–6 | 27 |
| $5b_3$ | $CH_3$ | $C(CH_3)_2CO_2Me$ | 1-methyl-3-piperidyl | 113–6 | 27 |
| $5c_1$ | $CH_3$ | $CH_2CO_2Me$ | 4-(2-hydroxyethyl)-piperazin-1-yl | 117–9 | 28 |
| $5c_2$* | $CH_3$ | $CH_2CO_2Et$ | 4-(2-hydroxyethyl)-piperazin-1-yl | oil | 28 |
| $5c_3$ | $CH_3$ | $C(CH_3)_2CO_2Et$ | 4-(2-hydroxyethyl)-piperazin-1-yl | oil | 28 |
| $5d_1$ | $CH_3$ | H | 4-(ethoxycarbonylmethyl)-piperazin-1-yl | 154–6 | 29 |
| $5d_2$ | $CH_3$ | ethyl | 4-(ethoxycarbonylmethyl)-piperazin-1-yl | 119–20 | 29 |
| $5e_1$ | $CH_3$ | $C(CH_3)_2CO_2Me$ | 1-acetylpiperazin-4-yl | 119–20 | 30 |
| $5e_2$ | $CH_3$ | $CH_2CO_2Me$ | 1-acetylpiperazin-4-yl | 137–9 | 30 |
| $5e_3$ | $CH_3$ | $CH_2CO_2Me$ | 4-morfolinyl | 149–50 | 30 |
| $5f_1$ | $CH_3$ | i-propyl | 4-(methoxycarbonylmethyl)-piperazin-1-yl | 120–2 | 31 |
| $5f_2$ | $CH_3$ | i-propyl | 4-(2,2-bis-(ethoxycarbonyl)-ethenyl)piperazin-1-yl | 128–9 | 31 |
| $5g_1$* | H | $C(CH_3)_2CO_2Me$ | 4-methylpiperazin-1-yl | 199–201 | 32 |
| $5g_2$* | H | $C(CH_3)_2CO_2Me$ | 4-morfolinyl | 175–7 | 32 |

*isolated as the hydrochloride.

TABLE 6

Compounds 6a–c

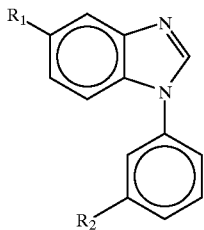

| Comp. No. | $R_1$ | $R_2$ | M.p. (° C.) | Start. Mat. | Method of Prep. (Ex.) |
|---|---|---|---|---|---|
| $6a_1$ | 5-isoxazolyl | $CO_2Me$ | 190–1 | | 33 |
| $6a_2$ | 5-isoxazolyl | $CO_2Et$ | 156–7 | | 33 |
| $6b_1$ | phenyl | $CO_2Et$ | 122–3 | 1e | 34 |
| $6b_2$ | phenyl | 4-(ethoxycarbonylmethyl)-piperazin-1-yl | 121–2 | 2e/1e | 34 |
| $6b_3$ | phenyl | 2-picolyloxycarbonyl | 149–50 | $6b_1$ | 35 |
| $6b_4$* | phenyl | 3-picolyloxycarbonyl | 195–7 | $6b_1$ | 35 |
| $6b_5$* | phenyl | (1-methyl-3-piperidyl)oxycarbonyl | 180–91 | $6b_1$ | 35 |
| $6b_6$* | phenyl | (1-methyl-4-piperidyl)-oxycarbonyl | 187–8 | $6b_1$ | 35 |
| $6c_1$ | 3-furanyl | $CO_2Et$ | 87–9 | 1d | 36 |
| $6c_2$* | 3-tetrahydrofuranyl | $CO_2Et$ | 168–71 | 1d | 36 |
| $6c_3$ | 3-furanyl | 4-(ethoxycarbonylmethyl)-piperazin-1-yl | 110–2 | 1d/2e | 36 |
| $6c_4$ | 3-furanyl | 4-(t-butoxycarbonyl)-piperazin-1-yl | 162–4 | 1d/2g | 36 |
| $6c_5$ | 3-furanyl | 4-(methoxycarbonylmethyl)-piperazin-1-yl | 124–5 | 1d/2l | 36 |
| $6c_6$ | 3-furanyl | 4-(2,2-bis(ethoxycarbonyl)-ethenyl)-piperazin-1-yl | 97–102 | 1d/2m | 36 |
| $6c_7$ | 3-furanyl | 4-(2-(methoxycarbonyl)-ethenyl)-piperazin-1-yl | 131–3 | 1d/2n | 36 |
| $6c_8$* | 3-furanyl | 2-(dimethylamino)-ethoxycarbonyl | 200–2 | 1d | 36 |

*isolated as the hydrochloride.

Example 1
Preparatory Example

4-Fluoro-3-nitroacetophenone (1b): Concentrated sulfuric acid (200 ml) is cooled to 5° C. 4-Fluoroacetophenone (20 ml, 0.16 mol) is added keeping the temperature below 10° C. The mixture is cooled to 0–5° C. and potassium nitrate (25 g, 0.25 mol) is added portionwise over 2 hours keeping the temperature within this range. Following the addition the mixture is stirred in the cold for additionally 2 hours. The mixture is poured on ice (600 g) and the crude product is filtered off. Column-chromatographic purification on silica gel using a mixture of ethyl acetate and petroleum ether (1:9) as the eluent affords pure 1 (18.2 g, 60%). Mp 48–49° C.

Example 2
Preparatory Example

Ethyl 4-chloro-3-nitrobenzoate (1c): 4-chloro-3-nitrobenzoic acid (40.0 g, 0.2 mol) was refluxed in thionyl chloride (150 ml) for 6 hours. After cooling toluene (50 ml) was added and the mixture was evaporated to dryness. Abs. ethanol (500 ml) was added to the cooled residue, and the resulting mixture was refluxed overnight. The excess of ethanol was removed under reduced pressure and the product crystallized upon addition of aqueous sodium bicarbonate (1M). Yield: 42.5 g (93%).

Example 3
Preparatory Example

4-Fluoro-1-iodo-3-nitrobenzene (1 g): A vigorously stirred suspension of 4-fluoro-3-nitroaniline (25 g, 0.16 mol) in conc. hydrochloric acid (125 ml) was cooled to −15° C. A solution of sodium nitrite (12.1 g, 0.18 mol) in water (25 ml) was added drop-wise keeping the temperature at −15° C. Following the addition the mixture was stirred for 15 min whereafter a solution of potassium iodide (33.4 g, 0.2 mol) in water (65 ml) was added over 45 min. At the end of the addition the mixture was stirred for additionally 30 min at ambient temperature. Aqueous sodium sulfite (1M) was added to remove iodine and the resulting mixture was extracted thrice with diethyl ether. The combined extracts were successively washed with ice-cold aqueous sodium hydroxide (1M) and brine, dried over sodium sulfate and concentrated under reduced pressure. The residue was purified by column chromatography on silica gel, using a mixture of ethyl acetate and petroleum ether (1:9 v/v) as the eluent, to yield the desired product (30.3 g, 71%) as a yellowish oil.

3-(4-Fluoro-3-nitrophenyl)furan (1d): A mixture of 1 g (25 g, 94 mmol), 3-furanyl-boronic acid (13.1 g, 117 mmol), potassium carbonate (38.8 g, 281 mmol), 1,3-propanediol (33.8 ml, 468 mmol) and tetrakis(triphenylphosphine)-palladium(0) (0.5 g) in a mixture of 1,2-dimethoxyethane passed through $Al_2O_3$ to remove peroxides (100 ml) and water (50 ml) was heated to reflux under nitrogen for 1 hour. The progress of the reaction was monitored by TLC using a mixture of ethyl acetate and petroleum ether (1:9 v/v) as the mobile phase. The mixture was poured into ice-water (500 ml). The precipitate was filtered off, washed with water and dissolved in ethyl acetate (200 ml). This solution was washed with cold 1 M HCl (3×100 ml) and brine. The organic phase was dried over $Na_2SO_4$ and evaporated to dryness to leave a crude product (100%). The crude product was dissolved in a mixture of dichlorometane and petroleum ether (1:1, v/v) and filtered through a short column (1.5 g silica gel per gram crude product). The column was washed with the above mixture (20 ml per gram crude product). The solvent was removed under reduced pressure and the residue was recrystallized (60° C.→0° C.) from 2-propanol (4 ml per gram residue).

Yield: 80%. M.p. 74.3–74.9° C. $^1$H NMR (DMSO-$d_6$): 7.11 ppm (s, 1H), 7.64 ppm (dd, 1H), 7.80 ppm (s, 1H), 8.06 ppm (m, 1H), 8.36 ppm (dd, 1H), 8.39 ppm (s, 1H).

4-Fluoro-3-nitrobiphenyl (1e) was prepared analogously from 1 g and phenylboronic acid.

Example 4
Preparatory Example

4-Fluoro-3-nitro-t-butylbenzene (1f): To a cold (5° C.) suspension of 4-t-butylaniline in a mixture of conc. hydrochloric acid (25 ml) and water (25 ml) was added a solution of sodium nitrite (7.6 g, 0.11 mol) in water (10 ml) keeping the temperature at 5–7° C. At the end of the addition, the mixture was stirred for additionally 15 min, whereafter a solution of sodium tetrafluoroborate (15.4 g, 0.14 mol) in water (30 ml) was added dropwise, maintaining the temperature at 5–8° C. After another 15 min at 5° C. the diazonium salt was filtered off, dried with suction and washed with diethyl ether (yield: 21 g). The diazonium salt was decomposed by gentle heating to 120° C. on an oil-bath. The product was distilled off and collected to yield 1f (11.2 g, 73.5%).

Example 5
Preparatory Example 3-(1-piperidyl)aniline (2a): A mixture of 3-fluoronitrobenzene (10.0 g, 70.9 mmol) and piperidine (14 ml, 141 mmol) was stirred at 110° C. for 3 days. After cooling water (200 ml) was added and the mixture was extracted with dichloromethane (3×100 ml). The combined organic extracts were washed with saturated aqueous sodium carbonate, dried over sodium sulfate and evaporated to dryness to leave 1-(3-nitrophenyl)piperidine (13.7 g, 93%) as an oil. This oil was dissolved in ethanol (150 ml) and was hydrogenated at ambient pressure using palladium on activated carbon as the catalyst to yield 2a (11.7 g, 100%) as an oil.

The following compounds were prepared analogously:
3-(1-pyrrolidinyl)aniline (2b);
3-(4-methyl-1-piperazinyl)aniline (2c); and
3-(4-morfolinyl)aniline (2o).

Example 6
Preparatory Example 3-(1-acetylpiperazin-4-yl)aniline (2d): A mixture of 3-fluoronitrobenzene (10.7 ml, 0.1 mol) and piperazine (43 g, 0.5 mol) in anhydrous NMP was heated to 115° C. for 2 days. After cooling the mixture was poured into water (200 ml) and extracted with ethyl acetate (3×50 ml). The combined organic extracts were washed with brine, dried over sodium sulfate and concentrated under reduced pressure. The residue was purified by column-chromatography on silica gel with a mixture of dichloromethane, methanol and aqueous ammonia (90:10:1 v/v/v) as the eluent to yield 1-(3-nitrophenyl)piperazine (17.2 g, 83%). This intermediate was acetylated with acetic acid anhydride (yield: 90%) and hydrogenated in methanol at ambient pressure using Pd (5% on activated carbon) as the catalyst to yield 2d (11.9 g, 74%) as off-white crystals.

In analogy herewith alkylation of 1-(3-nitrophenyl)piperazine with ethyl 2-bromoacetate, N,N-diethyl chloroacetamide, 2-bromoethanol, methyl 2-bromoacetate, diethyl ethoxymethylenmalonate and methylpropiolate followed by hydrogenation afforded respectively:
Ethyl 2-(4-(3-aminophenyl)piperazin-1-yl)acetate (2e);
N,N-diethyl 2-(4-(3-nitrophenyl)piperazin-1-yl) acetamide (2f);
3-(4-(2-hydroxyethyl)piperazin-1-yl)aniline (2k);
Methyl 2-(4-(3-aminophenyl)piperazin-1-yl)acetate (2l);
Diethyl (4-(3-aminophenyl)piperazin-1-yl)) methylenmalonate (2m); and
Methyl 2-(4-(3-aminophenyl)piperazin-1-yl)acrylate (2n).

Example 7
Preparatory Example 3-(1-(t-butoxycarbonyl)piperazin-4-yl)aniline (2g): A mixture of tert-butyl 1-piperazinecarboxylate (4 g, 21.5 mmol) and 3-fluoronitrobenzene (2.3 ml, 21.5 mmol) in anhydrous NMP (5 ml) was heated to 120° C. for 3 days. After cooling water (25 ml) was added and the mixture was extracted with ethyl acetate (2×10 ml). The organic extract was dried over sodium sulfate and the solvent was removed under reduced pressure. The residue was purified by column-chromatography using successively petroleum ether and a mixture of ethyl acetate and petroleum ether (1:1 v/v) as the eluents. Yield of t-butyl 4-(3-nitrophenyl)-1-piperazinecarboxylate: 1.34 g (20%). This intermediate was quantitatively hydrogenated to 2g in ethanol at ambient pressure using Pd (5% on activated carbon) as the catalyst.

The following compound was prepared analogously:
3-(1-methyl-4-homopiperazinyl)aniline (2h).

Example 8
Preparatory Example 3-((1-pyrrolidinyl)methyl)aniline (2i): To a solution of 3-nitrobenzylbromide (3 g, 13.9 mmol) in anhydrous THF (30 ml) was added a solution of pyrrolidine (2.3 ml, 27.8 mmol) in anhydrous THF (10 ml) dropwise with stirring. Following the addition the mixture was stirred at ambient temperature overnight. The reaction mixture was filtered, The filter cake was washed with a small volume of anhydrous THF and the filtrate was concentrated to leave the intermediate 1-(3-nitrobenzyl)pyrrolidine as an oil. This oil was dissolved in methanol (50 ml) and three equivalents of both ammonium chloride and sodium sulfide nonahydrate were added. The mixture was heated to reflux for 2 hours. After cooling the mixture was filtered. The filtercake was washed with methanol and the filtrate was concentrated under reduced pressure. The residue was dissolved in ethyl acetate and dried over sodium sulfate. Filtration and evaporation of solvent left 2i quantitatively as yellow crystals.

Example 9
Preparatory Example 3-(1-methyl-3-piperidinyl)aniline (2j): A mixture of 3-nitrophenylboronic acid (50 g, 0.3 mol), 3-bromopyridine (48 ml, 0.5 mol), potassium carbonate (207 g, 1.5 mol), 1,3-propanediol (107 ml, 1.5 mol) and tetrakis (triphenylphosphine)palladium(0) (0.5 g) in a mixture of water (200 ml) and dimethoxyethane (400 ml) was stirred in a nitrogen atmosphere at 80° C. for 3 hours. After cooling the dimethoxyethane was removed under reduced pressure and the residue was stirred with additionally 200 ml water overnight. The precipitate was filtered off and extracted with aqueous hydrochloric acid (4M, 300 ml). The extract was rendered alkaline by addition of aqueous sodium hydroxide (12M). The product was filtered off, washed with water and dried with suction to yield 3-(3-nitrophenyl)pyridine (50.6 g, 84%).

3-(3-nitrophenyl)pyridine (50 g, 0.25 mol) was added portion-wise with stirring to dimethyl sulfate (125 ml). The mixture was stirred at ambient temperature for 24 hours, during which time additional dimethyl sulfate was added (2×50 ml). At the end of the reaction diethyl ether (400 ml) was added, and the mixture was stirred in the cold for 2 hours. The precipitate was filtered off and washed several times with diethyl ether. Finally, the precipitate was stirred in pyridine (100 ml) at 45° C. for 30 min. THF (250 ml) was added. Stirring was continued for additionally 30 min whereafter the product was filtered off, washed with diethyl ether and dried to yield 1-methyl-3-(3-nitrophenyl) pyridinium methyl sulfate (66.6 g, 82%).

The above salt (66 g, 0.2 mol) was dissolved in methanol (750 ml) and sodium borohydride (11.4 g, 0.3 mol) was added in portions. At the end of the addition the mixture was filtered and the filtrate was concentrated under reduced pressure. The residue was partitioned between water and diethyl ether. The organic phase was dried over sodium sulfate and concentrated under reduced pressure. This concentrate was dissolved in ethanol (500 ml) and hydrogenated at ambient pressure using Pd (5% Pd on activated carbon) as the catalyst. Yield of 2j: 24.2 g (64%).

3-(3-Pyridyl)aniline (2p): A mixture of diethyl 3-pyridylborane (16.3 g, 0.11 mol), 3-bromoaniline (12.2 ml, 0.11 mol), potassium carbonate (45.8 g, 0.33 mol) and tetrakis(triphenylphosphine)palladium(0) (80 mg) in a mixture of water (40 ml) and dimethoxyethane (80 ml) is heated to 80° C. under a stream of nitrogen over night. After cooling the mixture is diluted with water and ethyl acetate and filtered through a fluted filterpaper. The layers are separated. The aqueous layer is extracted once with ethyl acetate. The combined organic phases are dried over sodium sulfate and concentrated under reduced pressure. The residue is dissolved in ethanol. Water is added and the mixture is evaporated to dryness. This residue crystallizes upon trituration with ice-cold water. The crystals are collected, dried and washed with petroleum ether to afford pure 2p (16.3 g, 87%). Mp 75–76° C.

Example 10

5-Cyano-1-(3-(1-Piperidyl)phenyl)benzimidazole ($3a_1$): A mixture of 4-chlor-3-nitrobenzonitril (5.0 g, 27.4 mmol), 2a (4.8 g, 27.4 mmol) and triethylamine (3.8 ml, 27.4 ml) in anhydrous NMP (5 ml) was heated with stirring to 120° C. under a stream of nitrogen overnight. After cooling the mixture was poured into water (50 ml). The crude product was filtered off, washed with water and dried with suction. Treatment with activated carbon in refluxing ethanol yielded pure N-(3-(1-piperidyl)phenyl)-4-cyano-2-nitroanilin (6.24 g, 71%).

This intermediate product (6.17 g, 19.1 mmol) was hydrogenated in ethanol at ambient pressure using Pd (5% on activated carbon) as the catalyst to yield the corresponding diamine (5.6 g, 100%), which was treated with formic acid (25 ml) at 80° C. for 1 hour. After cooling the mixture was poured into water (100 ml) and rendered alkaline by addition of saturated aqueous sodium carbonate. The product was filtered off and purified by treatment with activated carbon in refluxing ethanol followed by column-chromatography on silica gel using a mixture of ethyl acetate and petroleum ether (1:1 v/v) as the eluent. Yield of $3a_1$: 4.4 g (70%). M.p. 106–108° C.

The following compounds were prepared analogously:

5-Cyano-1-(3-(1-pyrrolidinyl)phenyl)benzimidazole ($3a_2$). M.p. 171–172° C.;

5-Cyano-1-(3-(4-methyl-1-piperazinyl)phenyl) benzimidazole ($3a_3$). M.p. 177–179° C.;

5-Cyano-1-(3-(1-methyl-3-piperidinyl)phenyl) benzimidazole, hydrochloride ($3a_4$). M.p. 158–160° C.; and 5-Cyano-1-(3-(4-morfolinyl)phenyl benzimidazole ($3a_5$). M.p. 163–165° C.

Example 11

5-Formyl-1-(3-(1-piperidinyl)phenyl)benzimidazole oxime ($3b_1$): To a solution of $3a_1$ (3.83 g, 12.9 mmol) in a mixture of formic acid (45 ml) and water (15 ml) was added Raney Ni (2.14 g, slurry in water). The mixture was refluxed with stirring for 3 hours. After cooling the mixture was filtered through celite and the filtrate was evaporated to dryness. The residue was partitioned between ethyl acetate and aqueous sodium bicarbonate (1M). The organic phase was dried over sodium sulfate and concentrated under reduced pressure. The concentrate was eluted through a short silica gel is column with ethyl acetate. Evaporation of the solvent left 5-formyl-1-(3-(1-piperidinyl)phenyl)-benzimidazole (3.86 g, 100%) as an oil. This oil was dissolved in refluxing ethanol (15 ml). Hydroxyl amine hydrochloride (2.64 g, 38.0 mmol) and triethylamine (1.70 ml) was added and reflux was continued for 5 hours. The cooled mixture was rendered basic by addition of triethylamine. Water was added and the pricipitate was filtered off, washed with water and dried to yield $3b_1$ (2.89 g, 70%). M.p. 213–214° C.

The following compounds were prepared analogously, using the appropriate hydroxylamines:

5-Formyl-1-(3-(1-pyrrolidinyl)phenyl)benzimidazole oxime ($3b_2$). M.p. 242–244° C.;

5-Formyl-1-(3-(4-methyl-1-piperazinyl)phenyl) benzimidazole oxime ($3b_3$). M.p. 224–227° C.;

5-Formyl-1-(3-(1-methyl-3-piperidinyl)phenyl) benzimidazole oxime ($3b_4$). M.p. 241–218° C.;

5-Formyl-1-(3-(1-piperidinyl)phenyl)benzimidazole O-isopropyl oxime (3c). M.p. 127–128° C.; and 5-Formyl-1-(3-(1-piperidinyl)phenyl)benzimidazole O-methyl oxime (3d). M.p. 107–108° C.

Example 12

5-Acetyl-1-(3-(1-acetylpiperazin-4-yl)phenyl) benzimidazole oxime ($3e_1$): A mixture of 1b (0.75 g, 4.1 mmol) and 2d (0.9 g, 4.1 mmol) in anhydrous NMP (2 ml) was heated to 80° C. overnight under a stream of nitrogen. After cooling water (20 ml) was added and the mixture was extracted with dichloromethane. The organic extract was dried over sodium sulfate and the solvent was removed under reduced pressure. The residue was purified by column-chromatography on silica gel using ethyl acetate as the eluent to yield 4-acetyl-N-(3-(1-acetylpiperazin-4-yl) phenyl)-2-nitroaniline as an oil.

This oil was dissolved in ethanol (25 ml) and was hydrogenated at ambient pressure using Pd (5% on activated carbon) as the catalyst. The resulting mixture was filtered through celite and the solvent was removed under reduced pressure. To the residue was added formic acid (5 ml) and the mixture was heated to 80° C. for 1 hour. After cooling water was added and the product was extracted with ethyl acetate. Column-chromatographic work-up on silica gel using a mixture of ethyl acetate and methanol (9:1) as the eluent yielded 5-acetyl-1-(3-(1-acetylpiperazinyl-4-yl) phenyl)benzimidazole (0.53 g, 36%). M.p. 112–114° C.

This product was treated with hydroxylamine hydrochloride in ethanol as described in Example 11 to yield $3e_1$ (90%). M.p. 240–242° C.

The following compounds were prepared analogously:

5-Acetyl-1-(3-(4-(2-hydroxyethyl)piperazin-1 -yl) phenylbenzimidazole oxime ($3e_2$). M.p. 193–195° C.;

5-Acetyl-1-(3-(4-(2-hydroxyethylpiperazin-1-yl) phenylbenzimidazole O-ethyl oxime ($3f_1$), $^1$H-NMR (CDCl$_3$, 500 MHz): 1.44 ppm (t, 3H), 2.43 ppm (s, 3H), 2.82 ppm (t, 2H), 2.92 ppm (m, 4H), 3.47 ppm (m, 4H), 3.83 ppm (t, 2H), 4.36 ppm (q, 2H), 7.07 ppm (m, 3H), 7.53 ppm (t, 1H), 7.59 ppm (d, 1H), 7.86 ppm (d, 1H), 8.15 ppm (s, 1H), 8.20 ppm (s, 1H);

5-Acetyl-1-(3-(4-methylpiperazin-1-yl)phenyl) benzimidazole O-ethyl oxime, hydrochloride ($3f_2$). M.p. 62–63° C. (oily crystals);

5-Acetyl-1-(3-(1-pyrrolidinylmethyl)phenyl) benzimidazole O-ethyl oxime, hydrochloride ($3f_3$). M.p. 158–162° C.;

5-Acetyl-1-(3-(4-methylhomopiperazin-1-yl) benzimidazole O-ethyl oxime, hydrochloride ($3f_4$). M.p. 147–151° C.;

5-Acetyl-1-(3-(1-pyrrolidinyl)phenyl)benzimidazole O-ethyl oxime ($3f_5$). M.p. 118–120° C.;

5-Acetyl-1-(3-(1-piperidinyl)phenyl)benzimidazole O-ethyl oxime ($3f_6$). M.p. 88–89° C.;

5-acetyl-1-(3-(1-methylpiperidin-3-yl)phenyl) benzimidazole O-ethyl oxime hydrochloride ($3f_7$). M.p. 112–114° C.;

5-Acetyl-1-(3-(1-methylpiperidin-3-yl)phenyl) benzimidazole O-isopropyl oxime, hydrochloride ($3g_1$). M.p. 48–55° C. $^1$H-NMR (CDCl$_3$, 500 MHz): 1.37 ppm (d, 6H), 1.75 ppm (qd, 1H), 2.08 ppm (d, 1H), 2.23 ppm (d, 1H), 2.34 ppm (s, 3H), 2.54 ppm (m, 1H), 2.80 ppm (m, 1H), 2.87 ppm (s+m, 4H), 3.64 ppm (t, 2h), 3.80 ppm (m, 1H), 4.50 ppm (hept., 1H), 7.43 ppm (d, 2H), 7.51 ppm (m, 3H), 7.61 ppm (t, 1H), 7.86 ppm (d, 1H), 8.13 ppm (s, 1H), 8.47 ppm (broad, 1H);

5-Acetyl-1-(3-(4-(2-hydroxyethyl)piperazin-1-yl)phenyl) benzimidazole O-isopropyl oxime, hydrochloride ($3g_2$). M.p. 165–169° C.;

5-Acetyl-1-(3-(4-acetylpiperazin-1-yl)phenyl) benzimidazole O-isopropyl oxime, hydrochloride (3 $g_3$). M.p. 160–163° C.; and 5-Acetyl-1-(3-(4-(2-hydroxyethyl)piperazin-1-yl)phenyl) benzimidazole O-t-butyl oxime (3h). $^1$H-NMR (CDCl$_3$, 500 MHz): 1.34 ppm (s, 9H), 2.25 ppm (s, 3H), 2.86 ppm (broad, 2H), 2.98 ppm (broad, 4H), 3.47 ppm (broad, 4H), 3.82 ppm (broad, 2H), 6.97 ppm (m, 3H), 7.44 ppm (m, 2H), 7.77 ppm (d, 1H), 8.06 ppm (s, 2H).

Example 12 a

5-Acetyl-1-[3-(1-methyl-1,2,3,6-tetrahydropyrid-5-yl)phenyl]benzimidazole O-ethyl oxime ($3f_8$)

4-Acetyl-N-(3-(3-pyridyl)phenyl-2-nitroaniline: A mixture of 1b from Example 1 (5 g, 27.3 mmol) and 2p from Example 9a (4.62 g, 27.2 mmol) in dry N-methyl-2-pyrrolidone (10 ml) is stirred at 40–50° C. over night. The resulting solid reaction mixture is suspended in ice-water and rendered alkaline by addition of aqueous sodium carbonate (1M). The product is filtered off, washed with water and dried to yield 7.68 g 4 (85%). Mp 112–113° C.

4-Acetyl-N-[3-(1-methylpyrid-3-ylium)phenyl]-2-nitroaniline methylsulfate (5):

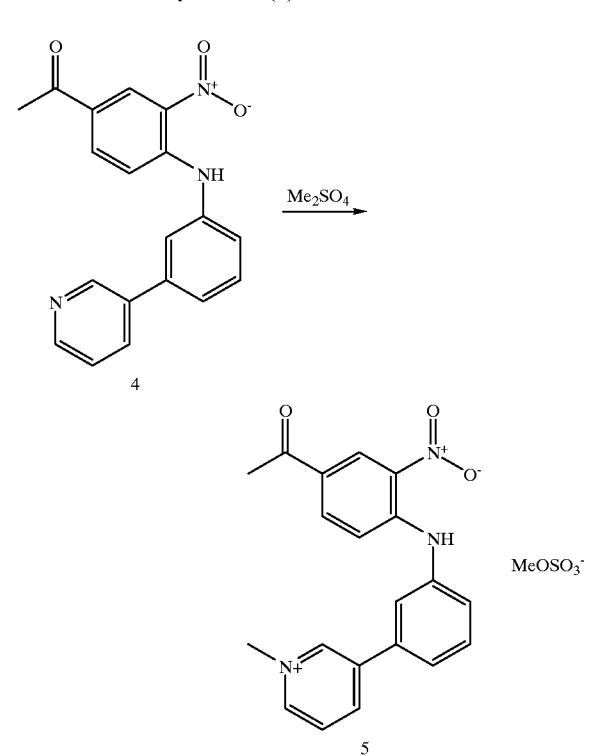

4-Acetyl-N-[3-(3-pyridyl)phenyl]-2-nitroaniline (4) (3.68 g, 11.05 mmol) in dimethyl sulfate (7.5 ml) was stirred at ambient temperature for 15 min. Diethyl ether was added and the mixture was stirred for additionally 30 min. The product was filtered off and dried to yield 4-acetyl-N-[3-(1-methylpyrid-3-ylium)phenyl]-2-nitroaniline methyl-sulfate (5) (4.9 g, 96.6%). Mp 118–125° C.

4-Acetyl-N-[3-(1-methyl-1,2,3,6-tetrahydropyrid-5-yl) phenyl]-2-nitroaniline (6):

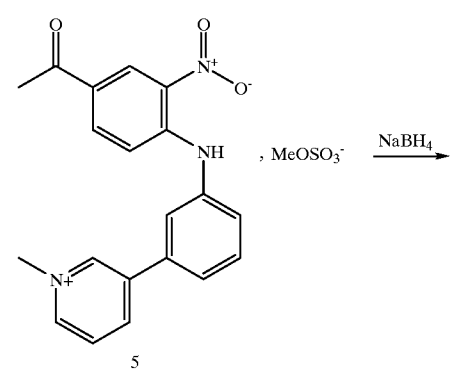

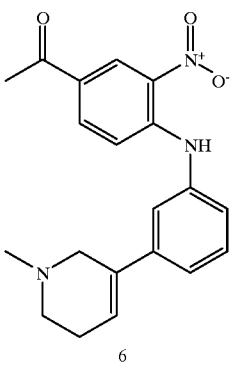

To a suspension of 4-acetyl-N-[3-(1-methylpyrid-3-ylium)phenyl]-2-nitroaniline methylsulfate (5) (4.9 g, 10.7 mmol) in methanol (50 ml) sodium borohydride (0.6 g, 16 mmol) was added portionwise with stirring. The resulting solution was stirred for 1 hour whereafter the solvent was removed by evaporation. The residue was partitioned between water and ethyl acetate. The organic phase was dried over sodium sulfate, concentrated under reduced pressure and purified by column chromatography on silica gel using a mixture of dichloromethane, methanol and acetone (4:1:1 v/v) as the eluent. Yield: 2.1 g (56%).

5-Acetyl-1 -[3-(1-methyl-1,2,3,6-tetrahydropyrid-5-yl)phenyl]benzimidazole (7):

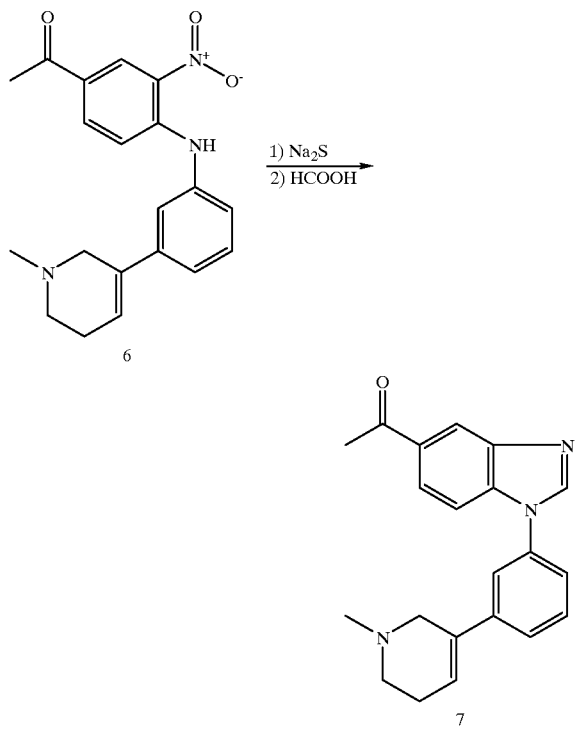

A mixture of 4-acetyl-N-[3-(1-methyl-1,2,3,6-tetrahydropyrid-5-yl)phenyl]-2-nitroaniline (5) (1 g, 3 mmol), sodium sulfide nonahydrate (4.32 g, 18 mmol) and ammonium chloride (0.96 g, 18 mmol) in methanol (50 ml) was heated to reflux over night. The solvent was removed under reduced pressure and the residue was partitioned between ethyl acetate and water. The organic phase was dried over sodium sulfate and concentrated to leave an oil (m/e: 321) which was stirred in formic acid (10 ml) at 80° C. for 4 hours. The resulting mixture was concentrated under reduced pressure. The residue was dissolved in water and filtered. The filtrate was rendered alkaline by addition of solid sodium carbonate and extracted with ethyl acetate. This extract was dried over sodium sulfate. Evaporation of the solvent left 5-acetyl-1-[3-(1-methyl-1,2,3,6-tetrahydropyrid-5-yl)phenyl]benzimidazole (7) as an oil. Yield: 0.5 g (50%), m/e: 331. A minor sample of this oil was dissolved in ethanol and precipitated as the hydrochloride by addition of hydrogen chloride in diethyl ether. Mp 227–233° C.

5-Acetyl-1-[3-(1-methyl-1,2,3,6-tetrahydropyrid-5-yl)phenyl]benzimidazole O-ethyl oxime (3f$_8$):

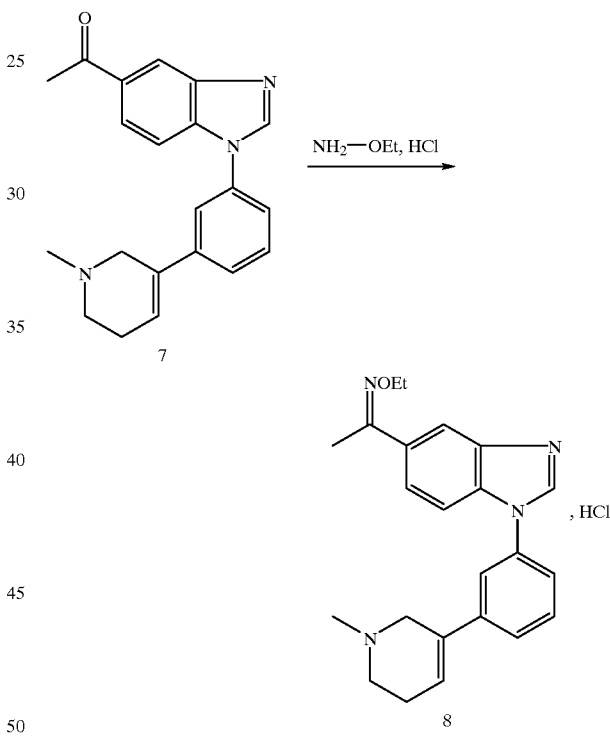

To a solution of 5-acetyl-1-[3-(1-methyl-1,2,3,6-tetrahydropyrid-5-yl)phenyl]benzimidazole (7) (free base from above) in ethanol was added O-ethyl hydroxylamine hydrochloride. The mixture was heated to reflux for 1.5 hours whereafter the solvent was removed under reduced pressure. The residue was triturated with a mixture of diethyl ether and ethanol leaving 5-acetyl-1-[3-(1-methyl-1,2,3,6-tetrahydropyrid-5-yl)phenyl]benzimidazole O-ethyl oxime (3f$_8$) as hygroscopic crystals. Mp 138–143° C., m/e 374.

Example 12 b

5-Acetyl-1-[3-(1-methylpiperidin-3-yl)phenyl]benzimidazole (9)

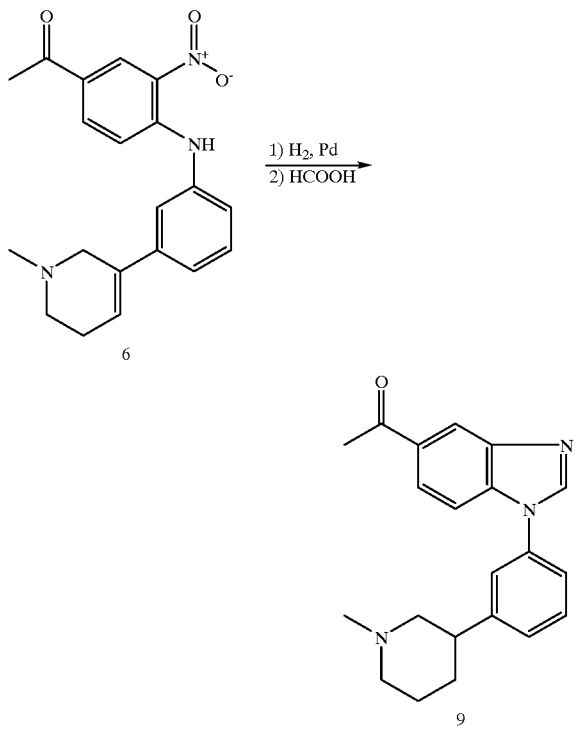

To a solution of 4-acetyl-N-[3-(1-methyl-1,2,3,6-tetrahydropyrid-5-yl)phenyl]-2-nitroaniline (6, Ex. 12a) (1 g, 3 mmol) in ethanol (50 ml) was added a catalytic amount of palladium on charcoal and the mixture was hydrogenated at ambient pressure over night. The reaction mixture was filtered through celite and the filtrate was concentrated under reduced pressure. To this concentrate formic acid (10 ml) was added and the resulting solution was stirred at 80° C. over night. Excess formic acid was removed by evaporation. The residue was dissolved in water and rendered alkaline by addition of solid sodium carbonate. Extraction with ethyl acetate and treatment of the extract with activated carbon in ethanol afforded 5-acetyl-1-[3-(1-methylpiperidin-3-yl)phenyl]-benzimidazole (9) (0.5 g, 50%) as an oil. m/e 333.

Example 13

5-(3-Furanyl)-1-(3-(4-methylpiperazin-1-yl)phenyl)benzimidazole ($3i_1$): A mixture of 1 g (1.4 g, 5.2 mmol) and 2c (1.0 g, 5.2 mmol) in anhydrous NMP (5 ml) was heated to 80° C. under a stream of nitrogen overnight. The mixture was poured into ice-water (50 ml) and rendered alkaline by addition of saturated aqueous sodium carbonate. The precipitate was filtered off and purified by column-chromatography on silica gel using a mixture of dichloromethane, methanol and aqueous ammonia (90:10:1 v/v/v) as the eluent. Yield of 4-iodo-2-nitro-N-(3-(4-methylpiperazin-1-yl)phenyl)aniline: 1.32 g (58%).

To a solution of the above product (1.3 g, 2.97 mmol) in a mixture of dimethoxyethane (20 ml) and water (10 ml) was added 3-furanylboronic acid (0.5 g, 4.45 mmol), potassium carbonate (1.23 g, 8.91 mmol), tetrakis(triphenylphosphine)palladium(0) (70 mg) and 1,3-propandiol (1.07 ml, 14.8 mmol). The resulting mixture was stirred under a stream of nitrogen at 80° C. for 6 hours. After cooling the mixture was filtered. The filtrate was diluted with water (50 ml) and extracted with ethyl acetate. The combined organic extracts were washed with brine, dried over sodium sulfate and evaporated to dryness to leave 4-(3-furanyl)-2-nitro-N-(3-(4-methylpiperazin-1-yl)phenyl)aniline (0.95 g, 85%) as a red oil.

This oil was hydrogenated at ambient pressure in ethanol using Pd (5% on activated carbon) as the catalyst to yield 2-amino-4-(3-furanyl)-N-(3-(4-methylpiperazin-1-yl)phenyl)aniline (0.6 g, 69%), which was treated with refluxing formic acid (5 ml) for 1 hour. After cooling the solution was poured into ice-water (25 ml) and aqueous sodium hydroxide (10M) was added to basic reaction. Extraction with ethyl acetate followed by chromatographic work-up on silica gel with a mixture of ethyl acetate and methanol (9:1 v/v) as the eluent left pure $3i_1$ (0.23 g, 41%). M.p. 129–130° C.

The following compounds were prepared analogously:

5-(3-Furanyl)-1-(3-(1-methylpiperidin-3-yl)phenyl)benzimidazole ($3i_2$). M.p. 96–97° C.;

5-(3-Furanyl)-1-(3-(4-(2-hydroxyethyl)piperazin-1-yl)phenyl)benzimidazole ($3i_3$). M.p. 137–140° C.;

5-(3-Furanyl)-1-(3-(4-(N,N-diethylcarboxamidomethyl)piperazin-1-yl)phenyl)benzimidazole ($3i_4$). M.p. 107–109° C.;

5-Phenyl-1-(3-(4-methylpiperazin-1-yl)phenyl)benzimidazole ($3j_1$). M.p. 131–132° C.; and 5-Phenyl-1-(3-(1-methylpiperidin-3-yl)phenyl)benzimidazole ($3j_2$). M.p. 42–44° C.;

In case of $3j_1$ and $3j_2$ phenylboronic acid was employed.

Example 14

5-(3-Cyclopropyl-1,2,4-oxadiazol-5-yl)-1-(3-(1-methylpiperidin-3-yl)phenyl)-benzimidazole, hydrochloride (3k): To a solution of sodium (0.1 g, 4 mmol) in anhydrous ethanol (10 ml) was added $4a_1$ (see example 16) (0.36 g, 1 mmol) and cyclopropylcar-boxamide oxime and the mixture was heated to reflux overnight. After removal of the solvent the residue was partitioned between water and ethyl acetate. The organic phase was dried over sodium sulfate and concentrated under reduced pressure. The product precipitated upon addition of a solution of anhydrous hydrogen chloride in diethyl ether. Yield of 3k: 0.2 g (46%). M.p. 184–190° C.

Example 15

5-t-Butyl-1-(3-(1-methylpiperidin-3-yl)phenyl)benzimidazole, hydrochloride (3l): A mixture of 1f (1.26 g, 6.9 mmol) and 2j (1.22 g, 6.4 mmol) in anhydrous NMP (2 ml) was heated with stirring in a nitrogen atmosphere to 80° C. overnight. Aqueous sodium carbonate was added to the cooled reaction mixture, and the resulting mixture was extracted with ethyl acetate. The organic phase was concentrated and purified by column-chromatography on silica gel using a mixture of ethyl acetate and methanol (9:1 v/v) as the eluent. Yield of 4-t-butyl-N-(3-(1-methylpiperidin-3-yl)phenyl)-2-nitroanilin (0.32 g, 14%) as an oil. This oil was dissolved in ethanol (15 ml) and was hydrogenated at ambient pressure using Pd (5% on activated carbon) as the catalyst to yield the corresponding phenylenediamine quantitatively. To a solution of this 2-amino-4-t-butyl-N-(3-(1-methylpiperidin-3-yl)phenyl)aniline in THF (5 ml) was added triethyl orthoformate (0.3 ml, 1.8 mmol) and a catalytic amount of pTSA. The resulting mixture was heated to reflux overnight. To the cooled solution aqueous sodium carbonate (1M) was added and the mixture was extracted with ethyl acetate. The organic extract was dried over sodium sulfate and evaporated to dryness. The residue was treated with a solution of anhygrous hydrogenchloride in diethyl ether to leave 3I (0.21 g, 63%) as a hygroscopic solid. M.p. approx. 200° C. (collapses at 70° C.). m/e: 347.

Example 16

5-(Ethoxycarbonyl)-1-(3-(1-methylpiperidin-3-yl) phenyl)benzimidazole, hydrochloride ($4a_1$): A mixture of 1c (5.7 g, 25 mmol), 2j (3.8 g, 20 mmol) and potassium carbonate (3.45 g, 25 mmol) was heated to 70° C. under a stream of nitrogen. The resulting melt was stirred at 70° C. overnight. The reaction mixture was partitioned between water and ethyl acetate and the organic phase was extracted with diluted hydrochloric acid (4M). The aqueous phase was rendered alkaline by addition of aqueous sodium hydroxide (4M) and extracted with ethyl acetate. The organic phase was dried over sodium sulfate and the solvent was removed under reduced pressure to leave ethyl 4-(3-(1-methylpiperidin-3-yl)phenylamino)-3-nitrobenzoate (7.5 g, 98%) as an oil.

The above oil was dissolved in ethanol (150 ml) and was hydrogenated at ambient pressure using Pd (5% on activated carbon) as the catalyst. The resulting phenylendiamine was treated with formic acid (25 ml) at 80° C. for 4 hours. Hereafter the excess formic acid was removed by evaporation. The residue was partitioned between aqueous sodium hydroxide (1M) and ethyl acetate. The organic phase was concentrated and purified by column-chromatography on silica gel using a mixture of dichloromethane, methanol and acetone (4:1:1 v/v/v) as the eluent. Evaporation of the solvent and treatment of the residue with a solution of anhydrous hydrogen chloride in diethyl ether (2M) left ($4a_1$) 5-(ethoxycarbonyl)-1-(3-(1-methylpiperidin-3-yl)phenyl) benzimidazole, hydrochloride (2.8 g, 35%) as a hygroscopic solid. $^1$H-NMR (DMSO-$d_6$, 500 MHz): 1.43 ppm (t, 3H), 1.47 ppm (m, 1H), 1.83 ppm (m, 2H), 2.00 ppm (m, 2H), 2.06 ppm (t, 1H), 2.34 ppm (s, 3H), 2.98 ppm (m, 3H), 4.40 ppm (q, 3H), 7.37 ppm (m, 3H), 7.50 ppm (m, 2H), 8.05 ppm (d, 1H), 8.17 ppm (s, 1H), 8.58 ppm (s, 1H).

The following compounds were prepared analogously:

5-(Ethoxycarbonyl)-1-(3-(4-methylpiperazin-1-yl) phenyl)benzimidazole ($4a_2$). M.p. 86–87° C.;

5-(Ethoxycarbonyl)-1-(3-(4-(2-hydroxyethyl)piperazin-1-yl)phenyl)benzimidazole, hydrochloride ($4a_3$). M.p. 233–236° C.;

5-(Ethoxycarbonyl)-1-(3-(1-acetylpiperazin-4-yl)phenyl) benzimidazole ($4a_4$). M.p. 155–156° C.;

5-(Ethoxycarbonyl)-1-(3-(4-(methoxycarbonylmethyl) piperazin-1-yl)phenyl)-benzimidazole, hydrochloride ($4a_5$). M.p. 185–186° C.; and 5-(Ethoxycarbonyl)-1-(3-(4-(ethoxycarbonylmethyl) piperazin-1-yl)phenyl)-benzimidazole, hydrochloride ($4a_6$). M.p. 196–200° C.

Example 17

5-(2-(Ethoxycarbonyl)ethenyl)-1-(3-(1-piperidyl)phenyl) benzimidazole ($4b_1$): To a suspension of sodiumhydride (70 mg, 60% dispersion in mineral oil) in anhydrous toluene (5 ml) was added triethyl phosphonoacetate (0.33 ml, 1.64 mmol), keeping the temperature at 30–35° C. Following the addition, stirring was continued until a clear solution had formed (approx. 15 min). A solution of 5-formyl-1-(3-(1-piperidinyl)-phenyl)benzimidazole (0.5 g, 1.64 mmol. Prepared as described in Example 11) in anhydrous toluene (2 ml) was added dropwise at 20–30° C. Following the addition the mixture was stirred at ambient temperature for 15 min and then at 60–65° C. for additional 15 min. Stirring was continued at ambient temperature overnight. The reaction mixture was decanted, leaving a rubber-like residue, which was extracted several times with toluene. The combined decantates were washed with water, dried over sodium sulfate and evaporated to dryness. The residue was triturated with petroleum ether to yield $4b_1$ (0.38 g, 61%). M.p. 85–87° C.

The following compounds were prepared analogously:

5-(2-(Ethoxycarbonyl)ethenyl)-1-(3-(4-methylpiperazin-1-yl)phenyl)benzimidazole ($4b_2$). M.p. 133–134° C.;

5-(2-(Ethoxycarbonyl)ethenyl)-1-(3-(4-morfolinyl) phenyl)benzimidazole ($4b_3$). M.p. 197–200° C.;

5-(2-(Methoxycarbonyl)ethenyl)-1-(3-(4-methylpiperazin-1-yl)phenyl)benzimidazole ($4c_1$). M.p. 138–140° C.; and 5-(2-(Methoxycarbonyl)ethenyl)-1-(3-(4-morfolinyl) phenyl)benzimidazole ($4c_2$). M.p. 137–139° C.

For the two latter preparations methyl diethyl phosphono acetate was employed.

Example 18

5-(Methoxycarbonyl)-1-(3-(1-acetylpiperazin-3-yl) phenyl)benzimidazole ($4d_1$): To a solution of methyl 4-chloro-3-nitrobenzoate (2.0 g, 9.28 mmol) in anhydrous NMP (5 ml) was added 2d (2.03 g, 9.28 mmol) and triethylamine (1.3 ml, 9.28 mmol). The mixture was heated with stirring to 80° C. overnight. The cooled solution was poured into ice-water (50 ml) and the resulting mixture was extracted with ethyl acetate (3×10 ml). The combined organic extracts were washed with water, dried over sodium sulfate and evaporated to dryness. The residue was triturated with petroleum ether to yield methyl 4-(3-(1-acetylpiperazin-4-yl)anilino)-3-nitrobenzoate (3.14 g, 85%) as red crystals.

This intermediate product was dissolved in methanol (50 ml) and was hydrogenated at ambient pressure using Pd (5% on activated carbon) as the catalyst to yield the corresponding diamino compound (2.8 g, 96%).

To a solution of this diamine in THF (50 ml) was added triethyl orthoformate (2.5 ml, 15.2 mmol) and a catalytic amount of pTSA. The mixture was heated to reflux for 1 hour. After cooling the solvent was removed by evaporation and the residue was partitioned between aqueous sodium carbonate (1M) and ethyl acetate. The organic phase was dried over sodium sulfate and concentrated under reduced pressure. The residue was purified by column-chromatography on silica gel using a mixture of ethyl acetate and methanol (9:1 v/v) as the eluent. Yield of $4d_1$: 5.52 (53%). M.p. 189–191° C.

The following compounds were prepared analogously:

5-(Methoxycarbonyl)-1-(3-(4-methylpiperazin-1-yl) phenyl)benzimidazole ($4d_2$). M.p. 119–121° C.;

4-(Methoxycarbonyl)-1-(3-(4-methoxycarbonylmethyl) piperazin-1-yl)benzimidazole ($4d_3$). $^1$H-NMR (CDCl$_3$, 500 MHz): 2.90 ppm (broad, 4H), 3.35 ppm (broad, 6H), 3.70 ppm (s, 3H), 3.90 ppm (s, 3H), 6.91 ppm (m, 2H), 6.95 ppm (d, 1H), 7.39 ppm (t, 1H), 7.48 ppm (d, 1H), 7.99 ppm (d, 1H), 8.11 ppm (s, 1H), 8.51 ppm (s, 1H);

5-(Methoxycarbonyl)-1-(3-(4-(N,N-diethylcarboxamidemethyl)piperazin-1-yl)phenyl)- benzimidazole (4d$_4$). $^1$H-NMR (CDCl$_3$, 500 MHz): 1.18 ppm (t, 3H), 1.26 ppm (t, 3H), 2.90 (broad, 4H), 3.42 ppm (m, 1 H), 3.99 ppm (s, 3H), 6.98 ppm (superimposed d+s, 2H), 7.04 ppm (d, 1H), 7.56 ppm (d, 1H), 8.07 ppm (d, 1H), 8.20 ppm (s, 1H), 8.60 ppm (s, 1H); and 5-(Methoxycarbonyl)-1-(3-(4-morfolinyl)phenyl) benzimidazole (4d$_5$). M.p. 150–152° C.

Example 19

5-(i-Propyloxycarbonyl)-1-(3-(1-piperidinyl)phenyl) benzimidazole (4e$_1$): To a mixture of isopropyl 4-chloro-3-nitrobenzoate (3.0 g, 12.3 mmol) and 2a (2.16 g, 12.3 mmol) in anhydrous NMP (5 ml) was added triethylamine (1.71 ml, 12.3 mmol) and the mixture was stirred at 80° C. under a stream of nitrogen overnight. The cooled mixture was partitioned between ethyl acetate and water. The organic phase was extracted with diluted hydrochloric acid (4M). The aqueous extract was rendered alkaline by addition of aqueous sodium hydroxide (12M) and extracted with ethyl acetate. This organic extract was dried over sodium sulfate and concentrated under reduced pressure. The residue was chromatographied on silica gel using a mixture of ethyl acetate and petroleum ether (1:1 v/v) as the eluent to yield isopropyl 3-nitro-4-(3-(1-piperidinyl)anilino)benzoate (2.55 g, 54%) as a red oil. This intermediate product was dissolved in ethanol (50 ml) hydrogenated at ambient pressure. The resulting diamine was treated with formic acid (25 ml) at 80° C. for 1 hour. The reaction mixture was poured into water (100 ml) and rendered alkaline by addition of aqueous sodium hydroxide (10M). The crude product was filtered off, washed with water and dried. Purification was achieved by treatment with activated carbon in refluxing 2-propanol followed by trituration with diethyl ether. Yield of 4e$_1$: 1.27 g (53%). M.p. 160–161° C.

The following compounds were prepared analogously:

5-(Methoxycarbonyl)-1-(3-(4-methylpiperazin-1-yl) phenyl)benzimidazole (4d$_2$). M.p. 119–121° C.;

4-(Methoxycarbonyl)-1-(3-(4-methoxycarbonylmethyl) piperazin-1-yl)benzimidazole (4d$_3$). $^1$H-NMR (CDCl$_3$, 500 MHz): 2.90 ppm (broad, 4H), 3.35 ppm (broad, 6H), 3.70 ppm (s, 3H), 3.90 ppm (s, 3H), 6.91 ppm (m, 2H), 6.95 ppm (d, 1H), 7.39 ppm (t, 1H), 7.48 ppm (d, 1H), 7.99 ppm (d, 1H), 8.11 ppm (s, 1H), 8.51 ppm (s, 1H);

5-(Methoxycarbonyl)-1-(3-(4-(N,N-diethylcarboxamidemethyl)piperazin-1-yl)phenyl)-benzimidazole (4d$_4$). $^1$H-NMR (CDCl$_3$, 500 MHz): 1.18 ppm (t, 3H), 1.26 ppm (t, 3H), 2.90 (broad, 4H), 3.42 ppm (m, 1H), 3.99 ppm (s, 3H), 6.98 ppm (superimposed d+s, 2H), 7.04 ppm (d, 1H), 7.56 ppm (d, 1H), 8.07 ppm (d, 1H), 8.20 ppm (s, 1H), 8.60 ppm (s, 1H); and 5-(Methoxycarbonyl)-1-(3-(4-morfolinyl)phenyl) benzimidazole (4d$_5$). M.p. 150–152° C.

Example 19

5-(i-Propyloxycarbonyl)-1-(3-(1-piperidinyl)phenyl) benzimidazole (4e$_1$): To a mixture of isopropyl 4-chloro-3-nitrobenzoate (3.0 g, 12.3 mmol) and 2a (2.16 g, 12.3 mmol) in anhydrous NMP (5 ml) was added triethylamine (1.71 ml, 12.3 mmol) and the mixture was stirred at 80° C. under a stream of nitrogen overnight. The cooled mixture was partitioned between ethyl acetate and water. The organic phase was extracted with diluted hydrochloric acid (4M). The aqueous extract was rendered alkaline by addition of aqueous sodium hydroxide (12M) and extracted with ethyl acetate. This organic extract was dried over sodium sulfate and concentrated under reduced pressure. The residue was chromatographied on silica gel using a mixture of ethyl acetate and petroleum ether (1:1 v/v) as the eluent to yield isopropyl 3-nitro-4-(3-(1-piperidinyl)anilino)benzoate (2.55 g, 54%) as a red oil. This intermediate product was dissolved in ethanol (50 ml) hydrogenated at ambient pressure. The resulting diamine was treated with formic acid (25 ml) at 80° C. for 1 hour. The reaction mixture was poured into water (100 ml) and rendered alkaline by addition of aqueous sodium hydroxide (10M). The crude product was filtered off, washed with water and dried. Purification was achieved by treatment with activated carbon in refluxing 2-propanol followed by trituration with diethyl ether. Yield of 4e$_1$: 1.27 g (53%). M.p. 160–161° C.

The following compounds were prepared analogously:

5-(i-Propyloxycarbonyl)-1-(3-(1-pyrrolidinyl)phenyl) benzimidazole (4e$_2$). M.p. 170–172° C.;

5-(i-Propyloxycarbonyl)-1-(3-(4-methylpiperazin-1-yl) phenyl)benzimidazole (4e$_3$). M.p. 110–111° C., and 5-(i-Propyloxycarbonyl)-1-(3-(4-morfolinyl)phenyl) benzimidazole (4e$_4$). M.p. 173–174° C.

Example 20

5-(Cyclopropylmethyloxycarbonyl)-1-(3-(1-methylpiperidin-3-yl)phenyl)benzimidazole (4f): To a solution of 4a$_1$ (1.5 g, 3.8 mmol) in ethanol (10 ml) was added aqueous potassium hydroxide (10 ml, 2M) and the mixture was heated to reflux for 2 hours. The ethanol was removed under reduced pressure, and the residue was neutralized by addition of acetic acid. The resulting amino acid was filtered off and dried. This product was suspended in toluene (100 ml). Thionylchloride (3 ml) was added, and the mixture was heated to 80° C. for 4 hours. The cooled mixture was evaporated to dryness, and the residue was suspended in anhydrous THF (60 ml).

To a part of the above suspension (20 ml) was added cyclopropylmethanol (0.8 ml, 10 mmol) and the mixture was stirred at room temperature for 5 days. The solvent was removed by evaporation and the residue was partitioned between aqueous sodium hydroxide (1M) and ethyl acetate. The organic phase was dried over sodium sulfate and evaporated to dryness. The residue was triturated with petroleum ether to yield 4f (30 mg, 7%). M.p. 111–113° C.

The following compounds were prepared analogously:

5-(Benzyloxycarbonyl)-1-(3-(1-methylpiperidin-3-yl) phenyl)benzimidazole, hydrochloride (4g). M.p. collapse at 90° C. M/e: 425; and 5-(3-Picolyloxycarbonyl)-1-(3-(1-methylpiperidin-3-yl) phenyl)benzimidazole (4h). $^1$H-NMR (CDCl$_3$, 500 MHz): 1.45 ppm (m, 1H), 1.8 ppm (broad, 2H), 2.1 ppm (broad, 3H), 2.4 ppm (broad, 3H), 3.0 ppm (broad, 3H), 5.36 ppm (s, 2H), 7.3 ppm (several signals, 4H), 7.45 ppm ("t", 2H), 7.77 ppm (d, 1H), 8.01 ppm (d, 1H), 8.12 ppm (s, 1H), 8.55 ppm (d, 1H), 8.57 ppm (s, 1H), 8.69 ppm (s, 1H).

Example 21

5-(2-((Dimethylamino)ethyl)oxycarbonyl)-1-(3-(1-acetylpiperazin-4-yl)phenyl)benzimidazole (4i): To a solution of 2-(dimethylamino)ethyl 4-chloro-3-nitrobenzoate (2.5 g, 9.1 mmol) and 2d (2.0 g, 9.1 mmol) in anhydrous NMP (5 ml) was added triethylamine (1.3 ml, 9.1 mmol), and the mixture was stirred at 80° C. for 4 hours. The cooled mixture was poured into ice-water (100 ml) and extracted with ethyl acetate (4×20 ml). The combined organic extracts were dried over sodium sulfate and concentrated under reduced pressure. The residue was purified by column-chromatography on silica gel using a mixture of dichloromethane and methanol (9:1 v/v) as the eluent to yield 2-(dimethylamino)ethyl 3-nitro-4-(3-(1-acetylpiperazin-4-yl)anilino)benzoate (1 g, 24%). This intermediate product was dissolved in ethanol (50 ml) and was hydrogenated quantitatively at ambient pressure, using Pd (5% on activated carbon) as the catalyst. The resulting diamine was dissolved in THF (50 ml) and triethyl orthoformate (0.7 ml, 4.2 mmol) was added, together with a catalytic amount of pTSA. The mixture was heated to reflux for 1 hour. The solvent was removed under reduced pressure and the residue was partitioned between aqueous sodium carbonate (1M) and ethyl acetate. The organic phase was dried over sodium sulfate and concentrated under reduced pressure, and the residue was chromatographied on silica gel using a mixture of dichloromethane, methanol and aqueous ammonia (90:10:1) as the eluent. The product isolated from the eluate was treated with activated carbon in refluxing ethanol and the product thus obtained was triturated with petroleum ether to yield 4i (0.18 g, 20%). M.p. 101–103° C.

The following compound was prepared analogously:

5-((2-(Dimethylamino)ethyl)oxycarbonyl)-1-(3-(4-(ethoxycarbonylmethyl)piperazin-1-yl)phenyl) benzimidazole (4j). $^1$H-NMR (CDCl$_3$, 500 MHz): 1.29 ppm (t, 3H), 2.44 ppm (s, 6H), 2.77 ppm (t, 4H), 2.88 ppm (t, 2H), 3.28 ppm (s, 2H), 3.33 ppm (t, 4H), 4.21 ppm (q, 2H), 4.54 ppm (t, 2H), 6.94 ppm (d, 1H), 6.96 ppm (s, 1H), 7.02 ppm (d, 1H), 7.44 ppm (t, 1H), 7.55 ppm (d, 1H), 8.06 ppm (d, 1H), 8.17 ppm (s, 1H), 8.58 ppm (s, 1H).

Example 22

5-((N,N-Diethylcarboxamido)methyloxycarbonyl)-1-(3-(4-ethoxycarbonylmethyl)-piperazin-1-yl)phenyl) benzimidazole (4k$_1$) and 5-((N,N-diethylcarboxamido)-methyloxycarbonyl)-1-(3-(1-acetylpiperazin-4-yl)phenyl) benzimidazole (4k$_2$): These compounds were prepared from (N,N-diethylcarboxamido)methyl 4-chloro-3-nitrobenzoate (1h) and 2e and 2d, respectively as described in Example 21.

1h was prepared as follows: To a solution of 4-chloro-3-nitrobenzoic acid (5.0 g, 24.8 mmol) in anhydrous DMF (25 ml) was added sodium iodide (0.37 g, 2.5 mmol), triethylamine (6.9 ml, 49.6 mmol) and 2-chloro-N,N-diethylacetamide (3.4 ml, 24.8 mmol). The resulting mixture was stirred at room temperature overnight. The mixture was poured into ice-water (100 ml) and the oily precipitate was filtered off and redissolved in ethyl acetate. This solution was dried over sodium sulfate and evaporated to dryness to yield 1h (7.46 g, 96%) as a yellow oil.

Example 23

4-Fluoro-3-nitrophenylacetic acid (1i): A suspension of 4-fluorophenylacetic acid (10.0 g, 64.9 mmol) in concentrated sulfuric acid (100 ml) was cooled to 0° C. Concentrated nitric acid (4.5 ml, 65 mmol) was added drop-wise, keeping the temperature at 0–5° C. At the end of the addition the mixture was poured into ice-water (400 ml). The precipitate was filtered off, washed thoroughly with water and dried with suction to yield 1i (9.11 g, 70%).

Example 24

5-(Methoxycarbonylmethyl)-1-(3-(4-methylpiperazin-1-yl)phenyl)benzimidazole, hydrochloride (4l$_1$): To a suspension of 1i (3.0 g, 15.1 mmol) in anhydrous NMP (2 ml) was added 2c (2.88 g, 15.1 mmol) and triethylamine (2.1 ml, 30.2 mmol). The mixture was stirred at 80° C. under a stream of nitrogen overnight. The cooled mixture was poured into a mixture of diethyl ether and petroleum ether (100 ml, 1:1 v/v) resulting in separation of an oily lower phase. The mixture was decanted and the oil was dissolved in dichloromethane and eluted through silica gel with a mixture of dichloromethane and methanol (4:1 v/v) to yield 3-nitro-4-(3-(4-methylpiperazin-1-yl)phenylamino)-phenylacetic acid (1.63 g, 29%). This acid (0.64 g, 1.73 mmol) was dissolved in methanol and concentrated hydrochloric acid (0.2 ml) was added. The mixture was heated to reflux for 4 days. The solvent was removed under reduced pressure and the residue was purified by column-chromatography on silica gel using a mixture of dichloromethane, methanol and aqueous ammonia (90:10:1 v/v/v) as the eluent to leave the ester (0.47 g, 71%) as a red oil. This oil was hydrogenated in methanol at ambient pressure using Pd (5% on activated carbon) as the catalyst to yield the corresponding diamine (0.38 g). This diamine was treated with triethyl orthoformate (0.35 ml, 2.14 mmol) and a catalytic amount of pTSA in THF (5 ml) at 80° C. for 30 min. The solvent was evaporated and the residue was partitioned between aqueous sodium hydroxide (1M) and ethyl acetate. The organic phase was dried over sodium sulfate, concentrated and eluted through a silica gel column with a mixture of dichloromethane, methanol and aqueous ammonia (90:10:1 v/v/v). The product precipitated as the hydrochloride by addition of a solution of anhydrous hydrogen chloride in diethyl ether to the eluate. Yield of 4l$_1$: 0.2 g (41%). M.p. 140–142° C.

The following compounds were prepared analogously:

5-(Ethoxycarbonylmethyl)-1-(3-(4-methylpiperazin-1-yl)phenyl)benzimidazole, hydrochloride (4l$_2$). M.p. 180–182° C.;

5-(Methoxycarbonyl)-1-(3-(4-morfolinyl)phenyl)benzimidazole, hydrochloride (4l$_3$). M.p. 164–165° C. Prepared from 1i and 2o; and 5-(Ethoxycarbonyl)-1-(3-(4-morfolinyl)phenyl)benzimidazole, hydrochloride (4l$_4$). M.p. 168–169° C. Prepared from 1i and 2o.

Example 25

5-((1-Methylpyrrolidin-2-yl)methoxycarbonyl)-1-(3-(4-(ethoxycarbonylmethyl)-piperazin-1-yl)phenyl) benzimidazole (4m) was prepared in analogy with Example 21 from (1-methylpyrrolidin-2-yl)methyl 4-chloro-3-nitrobenzoate and 2e. $^1$H-NMR (CDCl$_3$, 500 MHz): 1.10 ppm (t, 3H), 1.66 ppm (broad, 2H), 1.78 ppm (broad, 1H), 1.94 ppm (broad, 1H), 2.29 ppm (broad, 1H), 2.43 ppm (s, 3H), 2.60 ppm (t, 4H), 2.70 ppm (broad, 1H), 3.10 ppm (superimposed s, 2H and broad, 1H), 3.15 ppm (t, 4H), 4.02 ppm (q, 2H), 4.28 ppm (broad, 2H), 6.75 ppm (d, 1H), 6.78 ppm (s, 1H), 6.83 ppm (d, 1H), 7.24 ppm (t, 1H), 7.36 ppm (d, 1H), 7.87 ppm (d, 1H), 7.98 ppm (s, 1H), 8.38 ppm (s, 1H).

Example 26

5-Acetyl-1-(3-(1-methyl-4-piperidyloxycarbonyl)phenyl)benzimidazole O-isopropyl oxime (5a$_1$): A mixture 1b (11.0 g, 60.2 mmol), ethyl 3-aminobenzoate (9.9 g, 6.2 mmol) and triethylamine (8.34 ml, 60.2 mmol) in anhydrous NMP (5 ml) was heated to 130° C. with stirring under a stream of nitrogen for 4 hours. The cooled mixture was poured into ice-water (100 ml). Ethanol (10 ml) was added and the mixture was stirred until crystallization was completed. The precipitate was filtered off, washed with water and dried to yield ethyl (4-acetyl-2-nitrophenyl)aminobenzoate (19.1 g, 97%). This ester was hydrogenated quantitatively in a mixture of ethanol (400 ml) and dichloromethane (100 ml) using Pd (5% on activated carbon) as the catalyst. The resulting diamine was heated to reflux in formic acid (100 ml) for 1 hour. The cooled mixture was poured into ice-water (400 ml) and the precipitate was filtered off, washed with water and dried to yield 5-acetyl-1-(3-ethoxycarbonyl)phenylbenzimidazole (16.4 g, 91%).

The above ester (10 g, 32.5 mmol) was dissolved in dimethoxyethane (200 ml) and aqueous sodium hydroxide (100 ml, 1M) was added. The mixture was heated to 80° C. for 1 hour and the organic solvent was removed under reduced pressure. The residue was diluted with ice-water (100 ml) and mixture was neutralized by addition of glacial acetic acid. The precipitate was filtered off, washed with water and dried to yield 5-acetyl-1-(3-carboxyphenyl)benzimidazole (7.56 g, 83%).

This acid (4.66 g, 16.64 mmol) was suspended in anhydrous, peroxide free THF (50 ml) and heated to reflux. Carbonyldiimidazole (5.4 g, 33.28 mmol) was added in portions over 3 hours. Reflux was continued overnight. The solvent was removed under reduced pressure and the residue was triturated with diethyl ether to leave the crude 5-acetyl-1-(3-carboxyimidazolide)phenylbenzimidazole (6.9 g), contaminated with imidazole and carbonyldiimidazole.

To a solution of 1-methyl-4-hydroxypiperidine (1.06 ml, 9.1 mmol) in a mixture of anhydrous THF (5 ml) and anhydrous DMF (5 ml) was added sodium hydride (0.36 g 60% dispersion in mineral oil, 9.1 mmol) at ambient temperature. When the evolution of hydrogen had ceased, the above crude imidazolide (1.5 g) was added and the mixture was heated to 40° C. overnight. The cooled mixture was filtered and the filter-cake was washed with THF. The combined filtrate and washings was diluted with water and extracted with ethyl acetate. The organic extract was dried over sodium sulfate and concentrated by evaporation of solvent, and the residue was purified by column-chromatography using a mixture of dichloromethane, methanol and aqueous ammonia (90:10:1 v/v/v) as the eluent. This procedure yielded 5-acetyl-1-(3-(1-methyl-4-piperidyloxycarbonyl)phenyl)benzimidazole (0.56 g, 33%), which was treated with O-i-propylhydroxylamine, hydrochloride (0.17 g, 1.52 mmol) in refluxing ethanol (5 ml) overnight. Evaporation of solvent left a crude product, which upon column-chromatography in silica gel using a mixture of dichloromethane, methanol and aqueous ammonia (90:10:1 v/v/v) as the eluent yielded pure $5a_1$ (80 mg). M.p. 106–107° C.

The following compounds were prepared analogously:

5-Acetyl-1-(3-(1-methyl-3-piperidyloxycarbonyl)phenylbenzimidazole O-i-propyl oxime ($5a_2$). M.p. 83–84° C.; and 5-Acetyl-1-(3-(2-picolyloxycarbonyl)phenyl)benzimidazole O-i-propyl oxime ($5a_3$). M.p. 104–106° C.

Example 27

5-Acetyl-1-(3-(1-methylpiperidin-3-yl)phenyl)benzimidazole was prepared as described in Example 12. From this ketone the following O-alkylated oximes were prepared by treatment with the appropriate O-alkylated hydroxylamines under standard conditions:

5-Acetyl-1-(3-(1-methylpiperidin-3-yl)phenyl)benzimidazole O-(ethoxycarbonyl-methyl)oxime, hydrochloride ($5b_1$). M.p. 73–75° C.;

5-Acetyl-1-(3-(1-methylpiperidin-3-yl)phenyl)benzimidazole O-(methoxycarbonylmethyl)oxime ($5b_2$). M.p. 104–106° C.; and 5-Acetyl-1-(3-(1-methylpiperidin-3-yl)phenyl)benzimidazole O-(methoxycarbonyl-(dimethyl)methyl)oxime ($5b_3$). M.p. 113–115° C.

Example 28

5-Acetyl-1-(3-(4-(2-hydroxyethyl)piperazin-1-yl)phenyl)benzimidazole was prepared as described in Example 12. From this ketone the following O-alkylated oximes were prepared by treatment with the appropriate O-alkylated hydroxylamines under standard conditions:

5-Acetyl-1-(3-(4-(2-hydroxyethyl)piperazin-1-yl)phenyl)benzimidazole O-(methoxy-carbonylmethyl)oxime ($5c_1$). M.p. 117–119° C.;

5-Acetyl-1-(3-(4-(2-hydroxyethyl)piperazin-1-yl)phenyl)benzimidazol O-(ethoxy-carbonylmethyl)oxime, hydrochloride ($5c_2$). $^1$H-NMR (CDCl$_3$, 500 MHz): 1.23 ppm (t, 3H), 2.36 ppm (s, 3H), 2.66 ppm (t, 2H), 2.74 ppm (broad, 4H), 3.30 ppm (t, 4H), 3.67 ppm (t, 2H), 4.17 ppm (q, 2H), 4.70 ppm (s, 2H), 6.92 ppm ("m", 3H), 7.37 ppm (t, 1H), 7.43 (d, 1H), 7.67 ppm (d, 1H), 8.01 ppm (s, 1H), 8.05 ppm (s, 1H); and 5-Acetyl-1-(3-(4-(2-hydroxyethyl)piperazin-1-yl)phenyl)benzimidazole O-(ethoxy-carbonyl(dimethyl)methyl)oxime, hydrochloride ($5c_3$). $^1$H-NMR (DMSO-d$_6$, 500 MHz): 1.16 ppm (t, 3H), 1.52 ppm (s, 6H), 2.32 ppm (s, 3H), 3.11 ("m", 4H), 3.33 ppm (t, 2H), 3.60 ppm (d, 2H), 3.81 ppm ("s", 2H), 3.96 ppm (d, 2H), 4.12 ppm (q, 2H), 7.22 ppm (d, 1H), 7.25 ppm (d, 1H), 7.40 ppm (s, 1H), 7.78 ppm (d, 1H), 7.86 ppm (d, 1H), 8.08 ppm (s, 1H), 9.73 ppm (s, 1H), 11.00 ppm (broad, 1H).

Example 29

5-Acetyl-1-(3-(4-(ethoxycarbonylmethyl)piperazin-1-yl)phenyl)benzimidazole oxime ($5d_1$) was prepared from 1b and 2e under the conditions described in Example 12. M.p. 154–156° C.; and 5-Acetyl-1-(3-(4-(ethoxycarbonylmethyl)piperidin-1-yl)phenyl)benzimidazole O-ethyl oxime ($5d_2$). M.p. 119–120° C. was prepared analogously.

Example 30

5-Acetyl-1-(3-(1-acetylpiperazin-4-yl)phenyl)benzimidazole and 5-acetyl-1-(3-(4-morfolinyl)phenyl)benzimidazole were prepared as described in Example 12. From these ketones the following O-alkylated oximes were prepared by treatment with the appropriate O-alkyl hydroxylamines under standard conditions:

5-Acetyl-1-(3-(1-acetylpiperazin-4-yl)phenyl)benzimidazole O-(methoxycarbonyl-(dimethyl)methyl)oxime ($5e_1$). M.p. 119–120° C.;

5-Acetyl-1-(3-(1-acetylpiperazin-4-yl)phenyl)benzimidazole O-(methoxycarbonyl-methyl)oxime ($5e_2$). M.p. 137–139° C.; and 5-Acetyl-1-(3-(4-morfolinyl)phenyl)benzimidazole O-(methoxycarbonylmethyl)oxime ($5e_3$). M.p. 149–150° C.

Example 31

5-Acetyl-1-(3-(4-(methoxycarbonylmethyl)piperazin-1-yl)phenyl)benzimidazole O-i-propyl oxime ($5f_1$). To a solution of 5-acetyl-1-(3-(1-acetylpiperazin-4-yl)phenyl)benzimidazole (see Example 12) (8.3 g, 23.0 mmol) in dimethoxyethane (140 ml) was added aqueous sodium hydroxide (70 ml, 1M) and the mixture was heated to 80° C. overnight. The organic solvent was removed under reduced pressure and the residue was diluted with water and extracted with dichloromethane. The organic phase was concentrated and purified by column-chromatography on silica gel using a mixture of dichloromethane, methanol and aqueous ammonia (90:10:1 v/v/v) as the eluent. The concentrated eluate was triturated with diethyl ether to yield 5-acetyl-1-(3-(piperazin-1-yl)phenyl)benzimidazole (4.81 g, 65%) as red crystals. This product (2.0 g, 6.25 mmol) was dissolved in refluxing ethanol (20 ml). O-isopropylhydroxylamine, hydrochloride (0.7 g, 6.25 mmol) was added and reflux was continued for 5 hours. The reaction mixture was evaporated to dryness and the residue was partitioned between aqueous sodium hydroxide (1M) and dichloromethane. The organic phase was dried and concentrated and eluted through silica gel with a mixture of dichloromethane, methanol and aqueous ammonia (90:10:1 v/v/v) to yield 5-acetyl-1-(3-(1-piperazinyl)phenyl)-benzimidazole O-i-propyl oxime (1.75 g, 74%). This product was alkylated with methyl bromoacetate in anhydrous DMF on the presence of triethylamine at room temperature to yield $5f_1$ (0.48 g, 77%). M.p. 120–121° C.

Alkylation with diethyl ethoxymethylenemalonate afforded 5-acetyl-1-(3-(4-(2,2-bis(ethoxycarbonyl)ethenyl) piperazin-1-yl)phenyl)benzimidazole O-i-propyl oxime ($5f_2$). M.p. 128–129° C.

Example 32

5-Formyl-1-(3-(4-methylpiperazin-1-yl)phenyl) benzimidazole and 5-formyl-1-(3-(4-morfolinyl)phenyl) benzimidazole were prepared as described in Example 11. These aldehydes were condensed with O-(methoxycarbonyl (dimethyl) methyl)hydroxylamine under standard conditions to yield:

5-Formyl-1-(3-(4-methylpiperazin-1-yl)phenyl) benzimidazole O-(methoxycarbonyl-(dimethyl)methyl) oxime, hydrochloride ($5g_1$). M.p. 199–201° C.; and 5-Formyl-1-(3-(4-morfolinyl)phenyl)benzimidazole O-(methoxycarbonyl)dimethyl)-methyl) oxime, hydrochloride ($5g_2$). M.p. 175–177° C.

Example 33

5-(5-Isoxazolyl)-1-(3-(methoxycarbonyl)phenyl) benzimidazole ($6a_1$): To a suspension of 5-acetyl-1-(3-(methoxycarbonyl)phenyl)benzimidazole (prepared in analogy with Example 26) (0.6 g, 2.04 mmol) in anhydrous DMF (5 ml) was added dimethylformaldehyde dimethylacetal (0.43 ml, 3.24 mmol) and the mixture was heated to 120° C. under a stream of nitrogen overnight. The cooled mixture was poured into ice-water (25 ml) and the precipitate was filtered off and purified by column-chromatography on silica gel using a mixture of ethyl acetate and methanol (9:1 v/v) as the eluent to yield 5-(3-dimethylaminopropenoyl)-1-(3-(ethoxycarbonyl)phenyl)-benzimidazole (0.44 g, 62%).

The above intermediate (0.42 g, 1.2 mmol) was suspended in methanol (10 ml) and hydroxylamine, hydrochloride (0.21 g, 3 mmol) was added. The mixture was heated to reflux for 2 hours. The cooled mixture was poured into ice-water and the precipitate was filtered off, washed with water and dried. This crude product was chromatographied on silica gel using ethyl acetate as the eluent to yield $6a_1$ (0.2 g, 52%). M.p. 190–191° C.

The following compound was prepared analogously:

5-(5-Isoxazolyl)-1-(3-ethoxycarbonyl)phenyl benzimidazole ($6a_2$). M.p. 156–157° C.

Example 34

1-(3-Ethoxycarbonyl)phenyl-5-phenylbenzimidazole ($6b_1$): To a suspension of 1e (8.0 g, 36.9 mmol) and ethyl 3-aminobenzoate (6.1 g, 36.9 mmol) in anhydrous NMP (5 ml) was added triethylamine (5.1 ml, 36.9 mmol) and the mixture was stirred in a nitrogen atmosphere at 140° C. overnight. The cooled reaction mixture was diluted with water (50 ml) and extracted with ethyl acetate (3×20 ml). The organic extracts were dried over sodium sulfate and concentrated under reduced pressure. The product precipitated from the residue upon trituration with a mixture of diethyl ether and petroleum ether (1:1). Yield of ethyl N-(3-nitrobiphenyl-4-yl)aminobenzoate: 7.46 g (56%).

This ester was quantitatively hydrogenated in ethanol at ambient pressure using Pd (5% on activated carbon) as the catalyst. The resulting diamine was treated with formic acid (50 ml) at 80° C. for 1 hour. The cooled reaction mixture was poured into ice-water (200 ml) and was rendered alkaline by addition of aqueous sodium hydroxide (10M). The mixture was extracted with ethyl acetate and the extract was dried over sodium sulfate and evaporated to dryness. The residue was triturated with a mixture of petroleum ether and diethyl ether (9:1) to leave $6b_1$ (5.8 g, 85%). M.p. 122–123° C.

The following compound was prepared analogously from 1e and 2e:

5-Phenyl-1-(3-(4-ethoxycarbonylmethyl)piperazin-1-yl) phenyl)benzimidazole ($6b_2$). M.p. 121–122° C.

Example 35

5-Phenyl-1-(3-(2-Picolyloxycarbonyl)phenyl) benzimidazole ($6b_3$): To a solution of $6b_1$ (5.30 g, 15.5 mmol) in dimethoxyethane (100 ml) was added aqueous sodiumhydroxide (50 ml, 1M) and the mixture was heated to 40° C. for 2 hours. The organic solvent was removed by evaporation and the residue was diluted with an equal volume of water and acidified by addition of glacial acetic acid. The precipitate was filtered off, washed with water and dried to yield 5-phenyl-1-(3-carboxyphenyl)benzimidazole (4.26 g, 88%). M.p. 289–291° C.

This acid was treated with thionyl chloride (25 ml) at 80° C. for 2 hours. Excess thionyl chloride was removed by evaporation and the residue was triturated with diethyl ether to leave the corresponding carboxylic acid chloride, quantitatively.

To a suspension of the above carboxylic acid chloride (1.0 g, 3 mmol) in anhydrous THF (10 ml) was added 2-pyridylcarbinol (0.29 ml, 3 mmol) and the mixture was stirred in a nitrogen atmosphere at 40° C. overnight. The solvent was removed under reduced pressure, and the residue was stirred in aqueous sodium bicarbonate (1M). The precipitate was filtered off, washed with water and dried. Column-chromatography on silica gel using a mixture of ethyl acetate and methanol (9:1 v/v) as the eluent afforded $6b_3$ (0.29 g, 24%). M.p. 149–150° C.

The following compounds were prepared analogously:

5-Phenyl-1-(3-(3-picolyloxycarbonyl)phenyl) benzimidazole, hydrochloride ($6b_4$). M.p. 195–197° C.;

5-Phenyl-1-(3-(1-methylpiperid-3-yloxycarbonyl) phenyl)benzimidazole, hydrochloride ($6b_5$). M.p. 180–191° C.; and 5-Phenyl-1-(3-((1-methylpiperid-4-yl)oxycarbonyl) phenyl)benzimidazole, hydrochloride ($6b_6$). M.p. 187–188° C.

Example 36

5-(3-furanyl)-1-(3-(ethoxycarbonyl)phenyl) benzimidazole($6c_1$): To a solution of 1d (2.07 g, 10 mmol) in NMP (2 ml) was added ethyl 3-aminobenzoate (1.82 g, 11 mmol) and triethylamine and the mixture was heated to 110° C. in a nitrogen atmosphere overnight. The mixture was diluted with ice-water and extracted with ethyl acetate . The concentrated extract was purified by column-chromatography on silica gel using a mixture of petroleum ether and ethyl acetate (9:1 v/v) to yield ethyl 3-(N-(4-(3-furanyl)-2-nitrophenyl))aminobenzoate (1.18 g, 34%). This ester was hydrogenated in ethanol at ambient pressure using Pd (5% on activated carbon) as the catalyst. The resulting diamine (1.07 g) was treated with triethyl orthoformate (1.11 ml, 6.64 mmol) and a catalytic amount of pTSA in refluxing THF (10 ml). Column-chromatographic work-up of the concentrated reaction mixture using ethyl acetate as the eluent afforded $6c_1$ (0.66 g, 56%). M.p. 87–89° C.

From some preparations the following by-product was isolated:

5-(3-Tetrahydrofuranyl)-1-(3-(ethoxycarbonyl)phenyl) benzimidazole, hydrochloride ($6c_2$). M.p. 168–171° C.

The following compounds were prepared analogously from 1d and 2e, 2g, 2I, 2m, 2n and 2-(dimethylamino)ethyl 3-aminobenzoate, respectively:

5-(3-Furanyl)-1-(3-(4-(ethoxycarbonylmethyl)piperazin-1-yl)phenyl)benzimidazole ($6c_3$). M.p. 110–112° C.;

5-(3-Furanyl)-1-(3-(4-(t-butoxycarbonyl)piperazin-1-yl) phenyl)benzimidazole ($6c_4$). M.p. 162–164° C.;

5-(3-Furanyl)-1-(3-(4-(methoxycarbonylmethyl) piperazin-1-yl)phenyl)benzimidazole ($6c_5$). M.p. 124–125° C.;

5-(3-Furanyl)-1-(3-(4-(2,2-bis(ethoxycarbonyl)ethenyl) piperazin-1-yl)phenyl)-benzimidazole ($6c_6$). M.p. 97–102° C.;

5-(3-Furanyl)-1-(3-(4-(2-(methoxycarbonyl)ethenyl) piperazin-1-yl)phenyl)-benzimidazole ($6c_7$). M.p. 131–133° C.; and 5-(3-Furanyl)-1-(3-(2-(dimethylamino)ethyloxycarbonyl) phenyl)benzimidazole, hydrochloride ($6c_8$). M.p. 168–171° C.

Example 37

Biological Activity

Tissue Preparation: Preparations are performed at 0–4° C. unless otherwise indicated.

Cerebral cortex from male Wistar rats (150–200 g) is homogenized for 5–10 sec in 20 ml Tris-HCl (30 mM, pH 7.4) using an Ultra-Turrax homogenizer. The suspension is centrifuged at 27,000×g for 15 min, and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay: The membrane preparation is thawed and centrifuged at 2° C. for 10 min at 27,000×g. The pellet is washed twice with 20 ml 50 mM Tris-citrate, pH 7.1 using an Ultra-Turrax homogenizer and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

The test value is calculated as the $IC_{50}$ (the concentration (nM) of the test substance which inhibits the specific binding of $^3$H-FNM by 50%).

Test results obtained by testing selected compounds of the present invention appear from table 7, below.

TABLE 7

Biological Activity

| Test compound | $IC_{50}$ (µM) |
|---|---|
| 5-Acetyl-1-[3-(1-methylpiperidin-3-yl)-phenyl]benzimidazole O-ethyl oxime | 0.018 |
| 5-Cyano-1-(3-(1-pyrrolidinyl)phenyl)benzimidazole | 0,041 |
| 5-Formyl-1-(3-(1-methyl-3-piperidinyl)phenyl)benzimidazole oxime | 0,004 |
| 5-(3-Furanyl)-1-(3-(4-(2-hydroxyethyl)piperazin-1-yl) phenyl)benzimidazole | 0,005 |
| 5-(Ethoxycarbonyl)-1-(3-(4-(methoxycarbonylmethyl) piperazin-1-yl)phenyl)-benzimidazole, hydrochloride | 0,050 |
| 5-(3-Picolyloxycarbonyl)-1-(3-(1-methylpiperidin-3-yl) phenyl)benzimidazole | 0,080 |
| 5-(Methoxycarbonylmethyl)-1-(3-(4-methylpiperazin-1-yl) phenyl)benzimidazole, hydrochloride | 0,025 |
| 5-Acetyl-1-(3-(2-picolyloxycarbonyl)phenyl) benzimidazole O-i-propyl oxime | 0,002 |
| 5-Acetyl-1-(3-(4-(2-hydroxyethyl)piperazin-1-yl)phenyl) benzimidazole O-(methoxy-carbonylmethyl) oxime | 0,019 |
| 5-Acetyl-1-(3-(4-(ethoxycarbonylmethyl)piperidin-1-yl)phenyl) benzimidazole O-ethyl oxime | 0,027 |
| 5-(5-Isoxazolyl)-1-(3-ethoxycarbonyl)phenyl benzimidazole | 0,003 |
| 5-Phenyl-1-(3-(2-picolyloxycarbonyl)phenyl)benzimidazole | 0,008 |
| 5-(3-Furanyl)-1-(3-(4-(2,2-bis(ethoxycarbonyl)ethenyl) piperazin-1-yl)phenyl)-benzimidazole | 0,007 |

Penylenetetrazol (PTZ, Sigma) induces clonic convulsions in mice after i.v. infusion. Antagonism of penylenetetrazol-induced convulsions is considered predictive for drugs effective against various forms of epilepsia. The compounds of the present invention inhibits PTZ induced convulsions in mice at low doses.

Example 38

Biological Activity

In vivo inhibition of $^3$H-flunitrazepam ([3H]FNM) Binding

[$^3$H]FNM can be used for In vivo receptor labelling studies in mouse. Accumulation of [$^3$H]FNM binding will occur all over the brain as $GABA_A$ receptors are widely distributed. The specific binding of [$^3$H]FNM can be partly or completely prevented by simultaneous or prior administration of pharmacologically active benzodiazepines or by some benzodiazepine-like compounds.

Method: All test substances used are solutions prepared in 10% Tween 80. Groups of three female NMRI mice (25 g) are injected i.v. via the tail vein with 5.0 mCi of [3H]FNM in 0.2 ml saline. 15 min. after injection with [$^3$H]FNM the test substance is administered i.v. Twenty min after injection with [$^3$H]FNM, mice are killed by decapitation, the forebrains rapidly excised and homogenized in 12 ml of ice-cold 50 mM Tris-citrate, pH 7,1 using an Ultra-Turrax homogenizer. Three aliquots of 1 ml are immediately filtered through GF/C glass fiber filters and washed with 2×5 ml of ice-cold buffer.

The amounts of radioactivity on the filters and in 200 mL of the homogenate are determined by conventional scintillation counting. Groups of untreated mice serves as controls.

To determine non-specific binding groups of mice are injected with clonazepam (25 mg/kg) i.p. 10 min before [$^3$H]FNM injection. Specific binding is the amount of binding in controls minus the amount of binding in clonazepam treated mice.

Results: The $ED_{50}$ value is determined from dose response curves. The results show that the compounds of the present invention have a very favorable kinetic behavior.

What is claimed is:

1. A chemical compound represented by the formula (I):

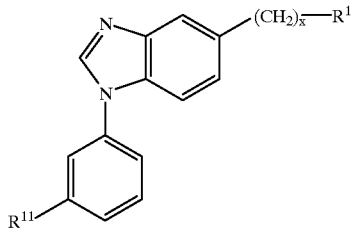

in which formula (I), x is 0, 1, 2 or 3;

$R^1$ represents a $C_{3-8}$-cycloalkyl group, a phenyl group, or a 5- or 6-membered monocyclic heterocyclic group, which groups are unsubstituted or substituted one or more times with substituents selected from the group consisting of $C_{1-8}$-alkyl, $C_{3-7}$-cycloalkyl, $C_{3-7}$-cycloalkyl-$C_{1-8}$-alkyl, alkoxy, halogen, trifluoromethyl, cyano, $NH_2$, $NH(C_{1-8}$-alkyl), $N(C_{1-8}$-alkyl)$_2$, and nitro;

or $R^1$ represents a cyano group, or a group of the formula —$C_{1-8}$-alkyl-$CO_2R^2$, $C_{2-6}$-alkenyl-$CO_2R^2$, —CO—$R^2$, —$CO_2(CH_2)_mR^2$, or —$C(R^3)$=N—$OR^2$, in which formulas m is 0, 1, 2 or 3;

$R^2$ and $R^3$ independently represents hydrogen, $C_{1-8}$-alkyl, $C_{3-7}$-cycloalkyl, $C_{2-6}$-alkenyl, $C_{2-6}$-alkynyl, phenyl, benzyl, or a 5- or 6-membered heterocyclic group, which heterocyclic group is unsubstituted or substituted one or more times with substituents selected from the group consisting of $C_{1-8}$-alkyl, $C_{3-7}$-cycloalkyl, hydroxy, alkoxy, halogen, trifluoromethyl, cyano, $NH_2$, $NH(C_{1-8}$-alkyl), $N(C_{1-8}$-alkyl)$_2$, and nitro;

or $R^2$ and $R^3$ independently represent a group of the formula —$(CH_2)_q$—$NR^4R^5$, —$(CH_2)_q$—$CON(R^4R^5)$, —$(CH_2)_q$—$CO_2R^4$, or —$C_{1-8}$-alkyl-$CO_2R^4$, in which formulas $R^4$ and $R^5$ independently represent hydrogen, $C_{1-8}$-alkyl, or $C_{3-7}$-cycloalkyl; and q is 0, 1, 2 or 3;

$R^{11}$ represents a group of the formula —$CO_2$—$R^9$, wherein $R^9$ represents $C_{1-8}$-alkyl, or $C_{3-7}$-cycloalkyl, which alkyl groups are unsubstituted or substituted with a 5- or 6-membered heterocyclic group, which heterocyclic group is unsubstituted or substituted one or more times with substituents selected from the group consisting of $C_{1-8}$-alkyl, $C_{3-7}$-cycloalkyl, hydroxy, alkoxy, halogen, trifluoromethyl, cyano, $NH_2$, $NH(C_{1-8}$-alkyl), $N(C_{1-8}$-alkyl)$_2$, and nitro;

or $R^9$ is a 5- or 6-membered heterocyclic group, which heterocyclic group is unsubstituted or substituted one or more times with substituents selected from the group consisting of $C_{1-8}$-alkyl, $C_{3-7}$-cycloalkyl, hydroxy, alkoxy, halogen, trifluoromethyl, cyano, $NH_2$, $NH(C_{1-8}$-alkyl), $N(C_{1-8}$-alkyl)$_2$, and nitro;

or $R^9$ represent a group of the -alkyl-$N(R^{10}R^{12})$, in which formula $R^{10}$ and $R^{12}$ independently represent hydrogen or $C_{1-8}$-alkyl, $C_{3-7}$-cycloalkyl;

or $R^{11}$ represents a group of formula (II):

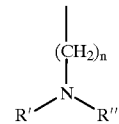

in which formula (II), n is 0, 1, 2, or 3;

R' and R" together with the N atom to which they are attached form a 5- or 6-membered heterocyclic ring, which heterocyclic ring has as a ring member, one or more members selected from the group consisting of one oxygen atom, one additional nitrogen atom and one —CH=CH— chain;

which heterocyclic ring is unsubstituted or substituted one or more times with a group of the formula —$(CH_2)_pX$, wherein p is 0, 1, 2 or 3;

X represents hydrogen, hydroxy, $C_{1-8}$-alkyl, $C_{3-7}$-cycloalky, or $C_{2-6}$-alkenyl, which alkyl, cycloalkyl or alkenyl groups are unsubstituted or substituted one or more times with a group of the formula —$CO_2R^6$;

or X represents a group of the formula —CO—$R^6$, —$CO_2$—$R^6$, —CON—$R^6R^7$, or —COO—$R^6$—$NR^7R^8$, in which formulas $R^6$, $R^7$ and $R^8$ independently represents hydrogen or $C_{1-8}$-alkyl, $C_{3-7}$-cycloalkyl;

or $R^{11}$ represents a group of the formula (III):

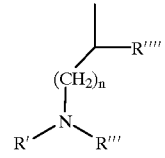

in which formula (III), n is 0, 1, 2 or 3;

R' is hydrogen, $C_{1-8}$-alkyl or $C_{3-7}$-cycloalkyl;

R'" and R"" together with the atoms to which they are attached form a 5- or 6-membered heterocyclic ring, which heterocyclic ring has as a ring member, one or more members selected from the group consisting of one oxygen atom, one additional nitrogen atom, and one —CH=CH— chain;

and in which formula the heterocyclic ring formed by R'" and R"" is unsubstituted or substituted one ore more times with the group of the formula —$(CH_2)_pX$, wherein p is 0, 1, 2 or 3;

X represents hydrogen, hydroxy, $C_{1-8}$-alkyl, $C_{3-7}$-cycloalkyl, or $C_{2-6}$-alkenyl, which alkyl, cycloalkyl or alkenyl groups are unsubstituted or substituted one or more times with a group of the formula —$CO_2R^6$;

or X represents a group of the formula —CO—$R^6$, —$CO_2$—$R^6$, —CON—$R^6R^7$, or —COO—$R^6$—$NR^7R^8$, in which formulas $R^6$, $R^7$ and $R^8$ independently represents hydrogen or $C_{1-8}$-alkyl, $C_{3-7}$-cycloalkyl;
or a pharmaceutically acceptable salt thereof or an oxide thereof;
provided, however, that $R^{11}$ is not 1-imidazolyl, 3-pyridyl, oxadiazolyl or morpholinyl.

2. The chemical compound according to claim 1, wherein x is 0; and
$R^1$ represents, a cyano group, a phenyl group, a furanyl group, a tetrahydrofuranyl group, an isoxazolyl group, or an oxadiazolyl group;
or $R^1$ represents a $C_{1-4}$-alkenyl group substituted with $CO_2$—$C_{1-4}$-alkyl;
or $R^1$ represents a group of the formula —$CO_2R^2$, in which formula
$R^2$ represents hydrogen, a $C_{1-4}$-alkyl group, or a —$C_{3-5}$-cyclo-$C_{1-4}$-alkyl group, a benzyl group, a picolyl group, a pyrrolidyl group, a pyrrolidyl-methyl group, or a pyridyl group, which groups are unsubstituted or substituted with a $C_{1-3}$-alkyl group;
or $R^2$ represents a group of the formula —$(CH_2)_q$—$NR^4R^5$, or —$(CH_2)_q$—CO—$NR^4R^5$, in which formulas q is 0, 1, or 2;
$R^4$ and $R^5$ each independently represents hydrogen or a $C_{1-4}$-alkyl group;
or $R^1$ may represent a group of the formula —$C(R^3)$=N—$OR^2$, in which formula
$R^3$ and $R^2$ each independently represents hydrogen or a $C_{1-4}$-alkyl group;
or $R^1$ represents a group of the formula —$C(R^3)$=N—$OR^4$, in which formula
$R^3$ represents hydrogen or a $C_{1-4}$-alkyl group;
and $R^4$ represents hydrogen, a $C_{1-4}$-alkyl group, or a $C_{1-4}$-alkyl-$CO_2$—$C_{1-4}$-alkyl group.

3. The chemical compound according to claim 1, wherein x is 0, 1, 2 or 3; and
$R^1$ represents a phenyl group, or a group of the formula —$CO_2R^4$, in which formula
$R^4$ represents hydrogen or a $C_{1-4}$-alkyl group.

4. The chemical compound according to claim 2, wherein x is 0; and
$R^1$ is 3-furanyl, 3-tetrahydro-furanyl, 5-isoxazolyl, 3-cyclopropyl-1,2,4-oxadiazol-5-yl, —CHNOH, —C(CH_3)NOH, —C(CH_3)NO—CH_3, —C(CH_3)NO—C_2H_5, —C(CH_3)NO-isopropyl, —C(CH_3)NO-t-butyl, —C(CH_3)NO—CH_2CO_2CH_3, —C(CH_3)NO—CH_2CO_2C_2H_5, —CHNO—C(CH_3)_2CO_2CH_3, —C(CH_3)NO—C(CH_3)_2CO_2CH_3, —C(CH_3)NO—C(CH_3)_2CO_2C_2H_5, —C(CH_3)_2CO_2CH_3, —C(CH_3)_2CO_2C_2H_5, —CO_2CH_3, —CO_2C_2H_5, —CO_2CH(CH_3)_2, —CO_2(CH_2)_2N(CH_3)_2, —CO_2(CH_2)_2N(C_2H_5)_2, —CO_2—CH_2-cyclopropyl, (N,N-diethyl-carboxamido)-methyl-oxycarbonyl, 3-picolyl, or 1-methyl-2-pyrrolidyl-methyl.

5. The chemical compound according to claim 3, wherein x is 1, 2 or 3; and
$R^1$ is —$CO_2CH_3$, —$CO_2C_2H_5$, —$CO_2CH(CH_3)_2$, —$CO_2CH_2$-cyclopropyl, —CHNO—CH_3, —CHNO—C_2H_5, —CHNO—C_3H_7, —CHNO-isopropyl, —C(CH_3)NO—CH_3, —C(CH_3)NO—C_2H_5, —C(CH_3)NO—C_3H_7, —C(CH_3)NO-isopropyl, —C(CH_3)NO—C_4H_9, —C(CH_3)NO-tert.butyl, —CO_2CH_2N(CH_3)_2, —CO_2CH_2N(C_2H_5)_2, 2(dimethyl-amino)ethyl, (N,N-diethyl-carboxamido)-methyl-oxycarbonyl, or 3-picolyl.

6. The chemical compound according to claim 1, wherein $R^{11}$ represents a $C_{1-4}$-alkyl-oxycarbonyl group, an amino-$C_{1-4}$-alkyl-oxycarbonyl group, an N—$C_{1-4}$-alkyl-amino-$C_{1-4}$-alkyl-oxycarbonyl group, or an N,N-di-$(C_{1-4}$-alkyl)-amino-$C_{1-4}$-alkyl oxycarbonyl group;
or $R^{11}$ represents a piperidinyl group, an piperidinyl-oxycarbonyl group, a pyrrolidinyl group, a pyrrolidinyl-$C_{1-3}$-alkyl group, a piperazinyl group, a homopiperazinyl group, a tetrahydropyridyl group, a picolyl-oxycarbonyl group, which groups are unsubstituted or substituted one or more times with substituents selected from the group consisting of $C_{1-4}$-alkyl, $C_{1-4}$-alkyl-oxy, $C_{1-4}$-alkyl-oxycarbonyl, $C_{1-4}$-alkyl-oxycarbonyl-$C_{1-4}$-alkyl, $C_{1-4}$-alkenyl-oxycarbonyl-$C_{1-4}$-alkyl, $C_{1-4}$-alkenyl-(oxycarbonyl-$C_{1-4}$-alkyl)_2, acetyl, hydroxy-$C_{1-4}$-alkyl, carboxamido, N—$C_{1-4}$-alkyl-carboxamido-$C_{1-4}$-alkyl, and N,N-di-$C_{1-4}$-alkyl-carboxamido-$C_{1-4}$-alkyl.

7. The chemical compound according to claim 6, wherein $R^{11}$ is 1-piperidinyl, 1-pyrrolidinyl, 4-methyl-1-piperazinyl, 1-methyl-3-piperidinyl, (1-methyl-4-piperidinyl)oxycarbonyl, (1-methyl-3-piperidinyl)oxycarbonyl, 2-picolyl-oxycarbonyl, 3-picolyl-oxycarbonyl, 4-morpholinyl, 1-acetyl-4-piperazinyl, 4-(2-hydroxyethyl)piperazin-1-yl, (1-pyrrolidinyl)methyl, 4-methylhomopiperazin-1-yl, 1-methyl-1,2,3,6-tetrahydropyrid-5-yl, 4-(N,N-diethyl-carboxamidomethyl)-piperazin-1-yl, 4-(N,N-dimethyl-carboxamidomethyl)-piperazin-1-yl, 4-(methoxycarbonylmethyl)-1-piperazinyl, 4-(ethoxycarbonylmethyl)-1-piperazinyl, 4-(t-butoxycarbonylmethyl)-1-piperazinyl, 4-(diethylcarboxamido-methyl)piperazin-1-yl, 4-(2,2-bis(ethoxycarbonyl)ethenyl)piperazin-1-yl, 4-(2-methoxycarbonyl-ethenyl)piperazin-1-yl, methoxycarbonyl, ethoxycarbonyl, 2-amino-ethoxycarbonyl, 2-(N-methylamino)ethoxycarbonyl, or 2-(N,N-dimethylamino)ethoxycarbonyl.

8. The chemical compound according to claim 1, which is,

5-Cyano-1-(3-(1-piperidyl)phenyl)benzimidazole (compound 3a);
5-Cyano-1-(3-(1-pyrrolidinyl)phenyl)benzimidazole (compound 3a_2);
5-Cyano-1-(3-(4-methyl-1-piperazinyl)phenyl)benzimidazole (compound 3a_3);
5-Cyano-1-(3-(1-methyl-3-piperidinyl)phenyl)benzimidazole (compound 3a_4);
5-Formyl-1-(3-(1-piperidinyl)phenyl)benzimidazole oxime (compound 3b_1);
5-Formyl-1-(3-(1-pyrrolidinyl)phenyl)benzimidazole oxime (compound 3b_2):
5-Formyl-1-(3-(4-methyl-1-piperazinyl)phenyl)benzimidazole oxime (compound 3b_3);
5-Formyl-1-(3-(1-methyl-3-piperidinyl)phenyl)benzimidazole oxime (compound 3b_4);
5-Formyl-1-(3-(1-piperidinyl)phenyl)benzimidazole O-isopropyl oxime (compound 3c);
5-Formyl-1-(3-(1-piperidinyl)phenyl)benzimidazole O-methyl oxime (compound 3d);
5-Acetyl-1-(3-(1-acetylpiperazin-4-yl)phenyl)benzimidazole oxime (compound 3e_1);
5-Acetyl-1-(3-(4-(2-hydroxyethyl)piperazin-1-yl)phenylbenzimidazole oxime (compound 3e_2);
5-Acetyl-1-(3-(4-(2-hydroxyethyl)piperazin-1-yl)phenylbenzimidazole O-ethyl oxime (compound 3f_1);
5-Acetyl-1-(3-(4-methylpiperazin-1-yl)phenyl)benzimidazole O-ethyl oxime (compound 3f_2);

5-Acetyl-1-(3-(1-pyrrolidinylmethyl)phenyl)benzimidazole O-ethyl oxime (compound $3f_3$);
5-Acetyl-1-(3-(4-methylhomopiperazin-1-yl)benzimidazole O-ethyl oxime (compound $3f_4$);
5-Acetyl-1-(3-(1-pyrrolidinyl)phenyl)benzimidazole O-ethyl oxime (compound $3f_5$);
5-Acetyl-1-(3-(1-piperidinyl)phenyl)benzimidazole O-ethyl oxime (compound $3f_6$);
5-Acetyl-1-(3-(1-methyl-3-piperidinyl)phenyl) benzimidazole O-ethyl oxime (compound $3f_7$);
5-Acetyl-1-(3-(1-methyl-1,2,3,6-tetrahydropyrid-5-yl) phenyl)benzimidazole O-ethyl oxime (compound $3f_8$);
5-Acetyl-1-(3-(1-methylpiperidin-3-yl)phenyl) benzimidazole O-isopropyl oxime (compound $3g_1$);
5-Acetyl-1-(3-(4-(2-hydroxyethyl)piperazin-1-yl)phenyl) benzimidazole O-isopropyl oxime (compound $3g_2$);
5-Acetyl-1-(3-(4-acetylpiperazin-1-yl)phenyl) benzimidazole O-isopropyl oxime (compound $3g_3$);
5-Acetyl-1-(3-(4-(2-hydroxyethyl)piperazin-1-yl)phenyl) benzimidazole O-t-butyl oxime (compound 3h);
5-(3-Furanyl)-1-(3-(4-methylpiperazin-1-yl)phenyl) benzimidazole (compound $3i_1$);
5-(3-Furanyl)-1-(3-(1-methylpiperidin-3-yl)phenyl) benzimidazole (compound $3i_2$);
5-(3-Furanyl)-1-(3-(4-(2-hydroxyethyl)piperazin-1-yl) phenyl)benzimidazole (compound $3i_3$);
5-(3-Furanyl)-1-(3-(4-(diethylcarboxamidomethyl) piperazin-1-yl)phenyl)benzimidazole (compound $3i_4$);
5-Phenyl-1-(3-(4-methylpiperazin-1-yl)phenyl) benzimidazole (compound $3j_1$):
5-Phenyl-1-(3-(1-methylpiperidin-3-yl)phenyl) benzimidazole (compound $3j_2$):
5-(3-Cyclopropyl-1,2,4-oxadiazol-5-yl)-1-(3-(1-methylpiperidin-3-yl)phenyl)-benzimidazole (compound 3k);
5-(Ethoxycarbonyl)-1-(3-(1-methylpiperidin-3-yl)phenyl) benzimidazole (compound $4a_1$);
5-(Ethoxycarbonyl)-1-(3-(4-methylpiperazin-1-yl)phenyl) benzimidazole (compound $4a_2$);
5-(Ethoxycarbonyl)-1-(3-(4-(2-hydroxyethyl)piperazin-1-yl)phenyl)benzimidazole (compound $4a_3$),
5-(Ethoxycarbonyl)-1-(3-(1-acetylpiperazin-4-yl)phenyl) benzimidazole (compound $4a_4$);
5-(Ethoxycarbonyl)-1-(3-(4-(methoxycarbonylmethyl) piperazin-1-yl)phenyl)-benzimidazole (compound $4a_5$);
5-(Ethoxycarbonyl)-1-(3-(4-(ethoxycarbonylmethyl) piperazin-1-yl)phenyl)benzimidazole (compound $4a_6$);
5-(2-(Ethoxycarbonyl)ethenyl)-1-(3-(1-piperidyl)phenyl) benzimidazole (compound $4b_1$);
5-(2-(Ethoxycarbonyl)ethenyl)-1-(3-(4-methylpiperazin-1-yl)phenyl)benzimidazole (compound $4b_2$);
5-(2-(Methoxycarbonyl)ethenyl)-1-(3-(4-methylpiperazin-1-yl)phenyl)benzimidazole (compound $4c_1$);
5-(Methoxycarbonyl)-1-(3-(1-acetylpiperazin-3-yl)phenyl) benzimidazole (compound $4d_1$);
5-(Methoxycarbonyl)-1-(3-(4-methylpiperazin-1-yl)phenyl) benzimidazole (compound $4d_2$);
4-(Methoxycarbonyl)-1-(3-(4-methoxycarbonylmethyl) piperazin-1-yl)benzimidazole (compound $4d_3$);
5-(Methoxycarbonyl)-1-(3-(4-(diethylcarboxamidemethyl) piperazin-1-yl)phenyl)-benzimidazole (compound $4d_4$);
5-(i-Propyloxycarbonyl)-1-(3-(1-piperidinyl)phenyl) benzimidazole (compound $4e_1$);
5-(i-Propyloxycarbonyl)-1-(3-(1-pyrrolidinyl)phenyl) benzimidazole (compound $4e_2$);
5-(i-Propyloxycarbonyl)-1-(3-(4-methylpiperazin-1-yl) phenyl)benzimidazole (compound $4e_3$);
5-(Cyclopropylmethyloxycarbonyl)-1-(3-(1-methylpiperidin-3-yl)phenyl)benzimidazole (compound 4f);
5-(Benzyloxycarbonyl)-1-(3-(1-methylpiperidin-3-yl) phenyl)benzimidazole (compound 4g);
5-(3-Picolyloxycarbonyl)-1-(3-(1-methylpiperidin-3-yl) phenyl)benzimidazole (compound 4h);
5-(2-((Dimethylamino)ethyl)oxycarbonyl)-1-(3-(1-acetylpiperazin-4-yl)phenyl)-benzimidazole (compound 4i);
5-((2-(Dimethylamino)ethyl)oxycarbonyl)-1-(3-(4-(ethoxycarbonylmethyl)piperazin-1-yl)phenyl) benzimidazole (compound 4j);
5-((N,N-Diethylcarboxamido)methyloxycarbonyl)-1-(3-(4-(ethoxycarbonylmethyl)-piperazin-1-yl)phenyl) benzimidazole (compound $4k_1$);
5-((N,N-diethylcarboxamido)-methyloxycarbonyl)-1-(3-(1-acetylpiperazin-4-yl)phenyl)benzimidazole (compound $4k_2$);
5-(Methoxycarbonylmethyl)-1-(3-(4-methylpiperazin-1-yl) phenyl)benzimidazole (compound $4l_1$);
5-(Ethoxycarbonylmethyl)-1-(3-(4-methylpiperazin-1-yl) phenyl)benzimidazole (compound $4l_2$);
5-((1-Methylpyrrolidin-2-yl)methoxycarbonyl)-1-(3-(4-(ethoxycarbonylmethyl)-piperazin-1-yl)phenyl) benzimidazole (compound 4m);
5-Acetyl-1-(3-(1-methyl-4-piperidyloxycarbonyl)phenyl) benzimidazole O-isopropyl oxime (compound $5a_1$);
5-Acetyl-1-(3-(1-methyl-3-piperidyloxycarbonyl)phenyl) benzimidazole O-i-propyl oxime (compound $5a_2$);
5-Acetyl-1-(3-(2-picolyloxycarbonyl)phenyl)benzimidazole O-i-propyl oxime (compound $5a_3$);
5-Acetyl-1-(3-(1-methylpiperidin-3-yl)phenyl) benzimidazole O-(ethoxycarbonyl-methyl) oxime (compound $5b_1$);
5-Acetyl-1-(3-(1-methylpiperidin-3-yl)phenyl) benzimidazole O-(methoxycarbonylmethyl, oxime (compound $5b_2$);
5-Acetyl-1-(3-(1-methylpiperidin-3-yl)phenyl) benzimidazole O-(methoxycarbonyl-(dimethyl)methyl) oxime (compound $5b_3$);
5-Acetyl-1-(3-(4-(2-hydroxyethyl)piperazin-1-yl)phenyl) benzimidazole O-(methoxy-carbonylmethyl) oxime (compound $5c_1$);
5-Acetyl-1-(3-(4-(2-hydroxyethyl)piperazin-1-yl)phenyl) benzimidazol O-(ethoxy-carbonylmethyl) oxime (compound $5c_2$);
5-Acetyl-1-(3-(4-(2-hydroxyethyl)piperazin-1-yl)phenyl) benzimidazole O-(ethoxy-carbonyl(dimethyl)methyl) oxime (compound $5c_3$);
5-Acetyl-1-(3-(4-(ethoxycarbonylmethyl)piperazin-1-yl) phenyl)benzimidazole oxime (compound $5d_1$);
5-Acetyl-1-(3-(4-(ethoxycarbonylmethyl)piperidin-1-yl) phenyl)benzimidazole O-ethyl oxime (compound $5d_2$);
5-Acetyl-1-(3-(1-acetylpiperazin-4-yl)phenyl) benzimidazole O-(methoxycarbonyl-(dimethyl)methyl) oxime (compound $5e_1$);
5-Acetyl-1-(3-(1-acetylpiperazin-4-yl)phenyl) benzimidazole O-(methoxycarbonyl-methyl) oxime (compound $5e_2$);
5-Acetyl-1-(3-(4-(methoxycarbonylmethyl)piperazin-1-yl) phenyl)benzimidazole O-i-propyl oxime (compound $5f_1$);
5-acetyl-1-(3-(4-(2,2-bis(ethoxycarbonyl)ethenyl) piperazin-1-yl)phenyl)benzimidazole O-i-propyl oxime (compound $5f_2$);
5-Formyl-1-(3-(4-methylpiperazin-1-yl)phenyl) benzimidazole O-(methoxycarbonyl-(dimethyl)methyl) oxime (compound $5g_1$);

5-(5-Isoxazolyl)-1-(3-(methoxycarbonyl)phenyl)benzimidazole (compound 6a$_1$);

5-(5-Isoxazolyl)-1-(3-ethoxycarbonyl)phenyl benzimidazole (compound 6a$_2$);

1-(3-Ethoxycarbonyl)phenyl-5-phenylbenzimidazole (compound 6b$_1$);

5-Phenyl-1-(3-(4-ethoxycarbonylmethyl)piperazin-1-yl)phenyl)benzimidazole (compound 6b$_2$);

5-Phenyl-1-(3-(2-picolylcxyarbonyl)phenyl)benzimioazole (compound 6b$_3$);

5-Phenyl-1-(3-(3-picolyloxycarbonyl)phenyl)benzimidazole (compound 6b$_4$);

5-Phenyl-1-(3-(1-methylpiperid-3-yloxycarbonyl)phenyl)benzimidazole (compound 6b$_5$);

5-Phenyl-1-(3-((1-methylpiperid-4-yl)oxycarbonyl)phenyl)benzimidazole (compound 6b$_6$);

5-(3-furanyl)-1-(3-(ethoxycarbonyl)phenyl)benzimidazole (compound 6c$_1$);

5-(3-Tetrahydrofuranyl)-1-(3-(ethoxycarbonyl)phenyl)benzimidazole (compound 6c$_2$);

5-(3-Furanyl)-1-(3-(4-(ethoxycarbonylmethyl)piperazin-1-yl)phenyl)benzimidazole (compound 6c$_3$);

5-(3-Furanyl)-1-(3-(4-(t-butoxycarbonyl)piperazin-1-yl)phenyl)benzimidazole (compound 6c$_4$);

5-(3-Furanyl)-1-(3-(4-(methoxycarbonylmethyl)piperazin-1-yl)phenyl)benzimidazole (compound 6c5);

5-(3-Furanyl)-1-(3-(4-(2,2-bis(ethoxycarbonyl)ethenyl)piperazin-1-yl)phenyl)-benzimidazole (compound 6c$_6$);

5-(3-Furanyl)-1-(3-(4-(2-(methoxycarbonyl)ethenyl)piperazin-1-yl)phenyl)-benzimidazole (compound 6c$_7$);

5-(3-Furanyl)-1-(3-(2-(dimethylamino)ethyloxycarbonyl)phenyl)benzimidazole (compound 6c$_8$);

5-Acetyl-1-[3-(1-methyl-1,2,3,6-tetrahydropyrid-5-yl)phenyl]-benzimidazole (compound 7); or 5-Acetyl-1-[3-(1-methylpiperidin-3-yl)phenyl]-benzimidazole (compound 9);

or a pharmaceutically acceptable salt thereof, or an oxide thereof.

9. A pharmaceutical composition comprising an effective amount of a chemical compound according to claim 1, or a pharmaceutically acceptable salt thereof, and a pharmaceutically acceptable excipient, carrier or diluent.

10. A method of treating a disease of a living animal body, including a human, which disease is responsive to modulation of the GABA$_A$ receptor complex of the central nervous system, which method comprises administration of a therapeutically effective amount of a chemical compound according to claim 1.

11. The method of claim 10, wherein the disease is responsive to positive modulation of the GABA$_A$ receptor complex of the central nervous system.

12. The method according to claim 10, wherein the disease is anxiety, anesthesia, epilepsy, or convulsions.

* * * * *